(12) United States Patent
Boynton

(10) Patent No.: US 9,445,932 B2
(45) Date of Patent: *Sep. 20, 2016

(54) ORTHOPEDIC SUPPORT GARMENT

(71) Applicant: Erin Lynn Boynton, Ontario (CA)

(72) Inventor: Erin Lynn Boynton, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 14/538,478

(22) Filed: Nov. 11, 2014

(65) Prior Publication Data

US 2015/0164672 A1 Jun. 18, 2015

Related U.S. Application Data

(63) Continuation of application No. 13/373,001, filed on Nov. 2, 2011, now Pat. No. 8,887,315.

(51) Int. Cl.
*A41D 13/00* (2006.01)
*A41D 27/02* (2006.01)
(Continued)

(52) U.S. Cl.
CPC ............ *A61F 5/0104* (2013.01); *A61F 5/026* (2013.01); *A63B 21/055* (2013.01); *A63B 23/12* (2013.01); *A41D 13/0015* (2013.01)

(58) Field of Classification Search
CPC .................. A41D 13/0015; A41D 2300/22; A41D 2400/38; A41D 27/00; A41D 13/015; A41D 13/1236; A41D 2400/32; A41D 31/02; A41D 13/0017; A41D 13/05; A41D 19/01582; A41D 1/00; A41D 1/084; A41D 31/00; A41D 13/0531; A41D 1/20; A41D 2400/00; A63B 21/1449; A63B 21/0552; A63B 21/0004; A63B 21/1419; A63B 21/055; A63B 21/1434; A63B 21/1442; A63B 21/1411; A63B 21/1415; A63B 21/0442; A63B 21/065; A63B 23/03575; A63B 69/0059; A41B 2400/38; A41B 1/08; A41B 2400/32; A41B 9/00; A41B 9/16; A61F 13/08; A61F 5/026; A61F 2005/0179; A61F 5/0102; A61F 5/028; A61F 5/0104; A61F 5/3738; A61F 5/3746; A61F 13/143; A61F 2013/0028; A61F 5/0109; A61F 5/0125; A61F 13/14; A61F 13/146; A61F 2002/5055; A61F 2002/5056; A61F 2013/00119; A61F 2/0045; A61F 5/02; A61F 5/03; A61H 2205/08; A61H 2201/1261; A61H 2201/165; A61H 2201/1654; A41C 1/06; A41C 3/0014; A41C 1/02; A41C 1/10; A41C 3/005; A41C 3/02; D03D 13/008; D03D 15/08; D03D 1/00; D03D 7/00; D03D 15/00; D03D 15/0044; D04B 21/18; D04B 21/207; D04B 1/18; D04B 1/246; D04B 1/26; D04B 21/00; D10B 2509/028; D10B 2401/046; D10B 2401/062; D10B 2401/061; A43B 13/181; A43B 1/04

USPC ........ 601/148, 149, 150, 151, 152; 128/24 R, 128/33, 64, 70, 680, 683, 668; 2/102, 456, 2/458, 2.11, 2.14, 2.17, 69, 905, DIG. 3, 2/81

See application file for complete search history.

(56) References Cited

U.S. PATENT DOCUMENTS 4,089,064 A 5/1978 Chandler, Jr.
4,091,466 A 5/1978 Kearn
(Continued)

OTHER PUBLICATIONS

Press release issued by Terra Public Relations, entitled "Opedix Introduces the Posture Shirt", Jul. 14, 2008.

*Primary Examiner* — Bobby Muromoto, Jr.
(74) *Attorney, Agent, or Firm* — Merchant & Gould P.C.

(57) ABSTRACT

An orthopedic garment includes a garment body made of stretchable fabric and configured to be worn in a form-fitting manner on the upper body of a wearer. The garment body has a front body portion, a rear body portion joined to the front body portion, and right and left sleeve portions attached to the front and rear body portions. Also provided is at least one tensor band laid out along one of the front and rear body portions in a manner intended to substantially correspond to at least one of the fascial lines extending along the upper body of the wearer. When the garment is worn by the wearer, the at least one tensor band may be placed in tension so as to provide proprioceptive feedback to the wearer during movement.

15 Claims, 19 Drawing Sheets

(51) Int. Cl.
*A61F 5/01* (2006.01)
*A61F 5/02* (2006.01)
*A63B 21/055* (2006.01)
*A63B 23/12* (2006.01)
*A41D 27/00* (2006.01)
*A41D 31/00* (2006.01)

(56) References Cited

U.S. PATENT DOCUMENTS

| | | | |
|---|---|---|---|
| 4,216,547 A | 8/1980 | Picchione | |
| 4,323,058 A * | 4/1982 | Detty | 602/27 |
| 4,488,314 A | 12/1984 | Johnson | |
| 4,625,336 A | 12/1986 | Derderian | |
| 4,685,153 A | 8/1987 | Sims | |
| 4,702,234 A | 10/1987 | Huntjens | |
| 4,735,572 A * | 4/1988 | Clifford | 434/247 |
| 4,850,056 A | 7/1989 | Gardner et al. | |
| 5,109,546 A | 5/1992 | Dicker | |
| 5,263,923 A | 11/1993 | Fujimoto | |
| 5,367,708 A | 11/1994 | Fujimoto | |
| 5,425,702 A * | 6/1995 | Carn et al. | 602/62 |
| 5,431,030 A | 7/1995 | Ishizaki et al. | |
| 5,571,039 A * | 11/1996 | Ford | 450/155 |
| 5,630,229 A | 5/1997 | Machado et al. | |
| 5,640,714 A | 6/1997 | Tanaka | |
| 5,659,895 A | 8/1997 | Ford, Jr. | |
| 5,727,254 A | 3/1998 | Dicker | |
| 5,735,807 A | 4/1998 | Cropper | |
| 5,737,773 A | 4/1998 | Dicker et al. | |
| 5,745,917 A | 5/1998 | Dicker et al. | |
| 5,782,790 A | 7/1998 | Allen | |
| 5,799,328 A * | 9/1998 | Harlem et al. | 2/69 |
| 5,829,058 A | 11/1998 | Dicker et al. | |
| 5,857,990 A * | 1/1999 | Maas | 602/62 |
| 5,867,826 A | 2/1999 | Wilkinson | |
| 5,875,491 A | 3/1999 | Wilkinson | |
| 5,937,441 A | 8/1999 | Raines | |
| 5,957,873 A | 9/1999 | Allen | |
| 5,978,966 A | 11/1999 | Dicker et al. | |
| 6,047,406 A | 4/2000 | Dicker et al. | |
| 6,053,852 A | 4/2000 | Wilkinson | |
| 6,086,551 A | 7/2000 | Allen | |
| 6,142,965 A | 11/2000 | Mathewson | |
| 6,186,970 B1 | 2/2001 | Fujii et al. | |
| 6,243,879 B1 | 6/2001 | Lyden | |
| 6,401,249 B2 | 6/2002 | Haar et al. | |
| 6,401,497 B1 | 6/2002 | Nishiyama et al. | |
| 6,440,094 B1 | 8/2002 | Maas | |
| 6,484,319 B1 | 11/2002 | Fusco et al. | |
| 6,546,560 B2 | 4/2003 | Fusco et al. | |
| 6,575,926 B2 | 6/2003 | Bonutti | |
| 6,945,945 B2 | 9/2005 | Givler et al. | |
| 7,134,969 B2 | 11/2006 | Citron et al. | |
| 7,156,792 B2 | 1/2007 | Gibson-Horn | |
| 7,229,390 B2 | 6/2007 | Fujii et al. | |
| 7,473,236 B1 | 1/2009 | Mathewson | |
| 7,516,498 B2 | 4/2009 | Torry | |
| 7,631,367 B2 | 12/2009 | Caillibotte et al. | |
| 7,730,552 B2 | 6/2010 | Ota et al. | |
| 7,814,576 B2 | 10/2010 | Nakazawa | |
| 7,900,284 B2 | 3/2011 | Mazzarolo | |
| 7,908,670 B2 | 3/2011 | Semba et al. | |
| 7,937,771 B2 | 5/2011 | Mazzarolo | |
| 7,945,970 B2 | 5/2011 | Belluye et al. | |
| 8,007,457 B2 | 8/2011 | Taylor | |
| 8,025,632 B2 | 9/2011 | Einarsson | |
| 8,047,893 B2 | 11/2011 | Fenske | |
| 8,095,994 B2 | 1/2012 | Natonson et al. | |
| 8,214,926 B2 | 7/2012 | Brown | |
| 8,347,415 B2 | 1/2013 | Mazzarolo | |
| 8,887,315 B2 | 11/2014 | Boynton | |
| 2002/0152546 A1 | 10/2002 | Durkin et al. | |
| 2003/0101506 A1 | 6/2003 | Fujii et al. | |
| 2004/0107479 A1 | 6/2004 | Dicker et al. | |
| 2004/0111781 A1 | 6/2004 | Miyake et al. | |
| 2004/0255358 A1 | 12/2004 | Ota et al. | |
| 2005/0193461 A1 | 9/2005 | Caillibotte et al. | |
| 2005/0197607 A1 | 9/2005 | Brown | |
| 2005/0239370 A1 | 10/2005 | Oyama et al. | |
| 2005/0240134 A1 | 10/2005 | Brown | |
| 2006/0169004 A1 | 8/2006 | Belluye et al. | |
| 2008/0222769 A1 | 9/2008 | Natonson et al. | |
| 2008/0222771 A1 | 9/2008 | Natonson et al. | |
| 2008/0319365 A1 | 12/2008 | Kendrick | |
| 2009/0062704 A1 | 3/2009 | Brown et al. | |
| 2009/0320180 A1 | 12/2009 | Torry | |
| 2012/0174282 A1 * | 7/2012 | Newton et al. | 2/69 |
| 2012/0191218 A1 * | 7/2012 | McCarthy | 623/34 |
| 2012/0204044 A1 * | 8/2012 | Bracken | 36/103 |
| 2012/0222187 A1 * | 9/2012 | McLaren et al. | 2/69 |
| 2012/0232448 A1 * | 9/2012 | Wust | 602/1 |
| 2012/0238923 A1 * | 9/2012 | Yamashita et al. | 601/46 |
| 2012/0245483 A1 * | 9/2012 | Lundqvist | 600/546 |
| 2012/0270708 A1 * | 10/2012 | Paulos | 482/124 |
| 2012/0296251 A1 * | 11/2012 | Delin | 602/26 |
| 2012/0310129 A1 * | 12/2012 | Johnson | 602/20 |
| 2013/0007946 A1 * | 1/2013 | Brown | 2/227 |
| 2013/0047313 A1 * | 2/2013 | Windisch et al. | 2/69 |
| 2013/0053744 A1 * | 2/2013 | Convert et al. | 602/26 |
| 2013/0053750 A1 * | 2/2013 | Taylor | 602/75 |
| 2013/0090521 A1 * | 4/2013 | Lau et al. | 600/30 |
| 2013/0090585 A1 * | 4/2013 | Bue et al. | 602/19 |
| 2013/0103079 A1 * | 4/2013 | Lau et al. | 606/229 |
| 2013/0111646 A1 * | 5/2013 | Sevenants | 2/69 |
| 2013/0172926 A1 | 7/2013 | Barker | 606/201 |
| 2013/0190895 A1 * | 7/2013 | Kristinsdottir | 623/36 |
| 2013/0211302 A1 * | 8/2013 | Brown | 602/19 |
| 2013/0232659 A1 * | 9/2013 | Levian | 2/69 |
| 2013/0253397 A1 * | 9/2013 | Samoodi | 602/19 |
| 2013/0263629 A1 * | 10/2013 | Gaither | 66/185 |
| 2013/0298306 A1 * | 11/2013 | Turner | 2/115 |
| 2013/0326785 A1 * | 12/2013 | Cornacchiari et al. | 2/69 |

* cited by examiner

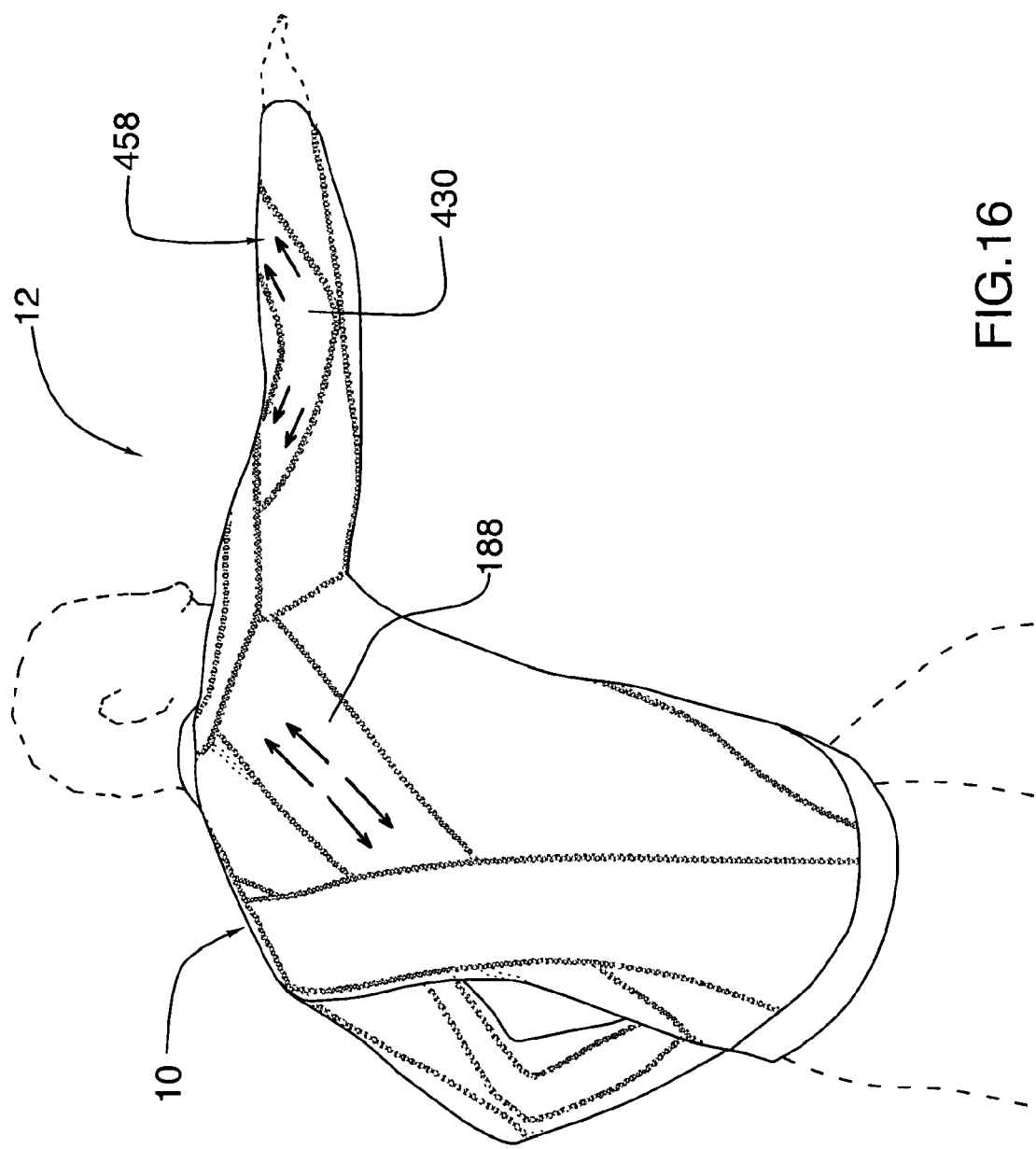

US 9,445,932 B2

ORTHOPEDIC SUPPORT GARMENT

CROSS REFERENCE TO RELATED APPLICATIONS

This application is a continuation application of U.S. application Ser. No. 13/373,001, filed Nov. 2, 2011, now U.S. Pat. No. 8,887,315, and titled "Orthopedic Support Garment," the disclosure of which is hereby incorporated herein by reference.

FIELD OF THE INVENTION

The present invention relates to the field of orthopedics, in particular, to an orthopedic support garment.

BACKGROUND OF THE INVENTION

Proper technique and coordinated muscle activation is critical for athletes seeking to perform biomechanical correct movements in sports. Athletes are constantly working on improving their proprioception—the sense of the relative position of neighbouring parts of the body and strength of effort being employed in movement—to master sport-specific movements. While there is no substitute for proper conditioning and training, certain aids have been developed to assist athletes with the enhancement of proprioception.

In some cases, such aids have come in the form of a garment to be worn by the athlete during the performance of certain movements. In its most basic form, such a garment may be made of a stretchable or elastic fabric and is intended to be worn tightly on the body in a form-fitting manner (in some cases, this garment is fashioned as compression garment). Because of the resistance encountered by the wearer as a result of the stretch in the fabric, the wearer tends to become more aware of the relative position of his limbs. While this type of garment can enhance proprioception, it tends not to be anatomically focused and thus tends not to perform a genuine orthopedic function.

United States Patent Application Publication No. US 2009/0062704 of Brown et al. provides an example of a garment designed specifically for proprioceptively treating a wearer. The garment is preferably configured like a short-sleeved undershirt or T-shirt and may be fabricated of a stretchable material to achieve the desired form-fitting fit. The garment includes an anterior portion and a posterior portion joined to the anterior portion. Each of the anterior portion and the posterior portion are fabricated of a thin, elastomeric material. The material used is form-fitting to allow pressure to be applied to the surface of the wearer's skin to enhance neuromuscular stimulation. Integrated with the posterior garment portion, is a proprioceptive panel. This panel is positioned to extend over the upper back or inter scapular region of the wearer. In one embodiment, the proprioceptive panel is positioned to extend along substantially an entire length of the spine of the wearer. In still another embodiment, the proprioceptive panel is generally triangular in shape, and is positioned to extend downwardly from the shoulders of the wearer toward an apex positioned to be disposed at approximately the small of the wearer's back. The proprioceptive panel may be fabricated of the same elastomeric material as the posterior portion or may be made of a heavier, more dense elastomeric material than that used for the posterior portion.

The garment described in United States Patent Application Publication No. US 2009/0062704 of Brown et al. appears to be specifically configured to enhance proprioception in the wearer for the purposes of improving or enhancing posture. To this end, it uses strategically placed proprioceptive panels that primarily target muscles and other anatomical structures of the wearer's back. While this garment may be effective at providing some back support and may assist in the improvement of the wearer's posture, it tends to be too narrowly focused on the muscles of the back to be a useful aid to athletes performing complex movements which recruit other muscle groups of the upper body.

Accordingly, there is a genuine need for a garment which is capable of providing enhanced anatomically appropriate proprioceptive (and kinesthetic) feedback to the wearer for various muscle groups of the upper body, including those of the chest, back, shoulders and arms. Advantageously, such a garment could help athletes perfect their technique or form in performing complex sport-specific movements which recruit multiple muscle groups of the upper body. A garment of this nature would tend to be a very versatile aid to athletes.

SUMMARY OF THE INVENTION

According to a broad aspect of an embodiment of the present invention, there is provided an orthopedic support garment. The orthopedic garment includes a garment body made of stretchable fabric and configured to be worn in a form-fitting manner on the upper body of a wearer. The garment body has a front body portion, a rear body portion joined to the front body portion, and right and left sleeve portions attached to the front and rear body portions. Also provided is at least one tensor band laid out along one of the front and rear body portions in a manner intended to substantially correspond to at least one of the fascial lines extending along the upper body of the wearer. When the garment is worn by the wearer, the at least one tensor band may be placed in tension so as to provide proprioceptive (and kinesthetic) feedback to the wearer during movement.

In another feature, the at least one tensor band includes a first tensor band and a second tensor band. The first and second tensor bands are disposed in a crosswise fashion along the front body portion in a manner intended to substantially correspond to the front functional line extending along the upper body of the wearer.

In a further feature, the garment body further includes a waistband attached along the lower margins of the front and rear body portions. The first tensor band extends between the waistband and the juncture of the right sleeve and front body portions. The second tensor band extends between the waistband and the juncture of the left sleeve and front body portions.

In an additional feature, the first and second tensor bands are made from a plurality of fabric panels. Alternatively, the first and second tensor bands are made from a single fabric panel.

In yet another feature, the at least one tensor band includes a third tensor band. The third tensor band is disposed vertically along the front body portion at a location intended to substantially correspond to the superficial front line extending along the upper body of the wearer.

In still another feature, the at least one tensor band is disposed diagonally across the front body portion in a manner intended to substantially correspond to one of the fascial lines that make up the front functional line which extends along the upper body of the wearer. In one feature, the garment body further includes a waistband attached along the lower margins of the front and rear body portions.

The at least one tensor band extends between the waistband and the juncture of the right sleeve and front body portions. In an alternate feature, the at least one tensor band extends between the waistband and the juncture of the left sleeve and front body portions.

In an additional feature, the at least one tensor band includes a first tensor band and a second tensor band. The first and second tensor bands are disposed in a crosswise fashion along the rear body portion in a manner intended to substantially correspond to the back functional line extending along the upper body of the wearer. The garment body further includes a waistband attached along the lower margins of the front and rear body portions. The first tensor band extends between the waistband and the juncture of the right sleeve and rear body portions. The second tensor band extends between the waistband and the juncture of the left sleeve and rear body portions.

In one feature, the first and second tensor bands are made from a plurality of fabric panels. In an alternate feature, the first and second tensor bands are made from a single fabric panel.

In still another feature, the at least one tensor band includes a third tensor band. The third tensor band is disposed vertically along the rear body portion at a location intended to substantially correspond to the superficial back line extending along the upper body of the wearer.

In yet another feature, the at least one tensor band is disposed diagonally across the rear body portion in a manner intended to substantially correspond to one of the fascial lines that make up the rear functional line which extends along the upper body of the wearer.

In a further feature, the garment body further includes a waistband attached along the lower margins of the front and rear body portions. The at least one tensor band extends between the waistband and the juncture of the right sleeve and rear body portions. In an alternate feature, the at least one tensor band extends between the waistband and the juncture of the left sleeve and rear body portions.

In another feature, the at least one tensor band includes first and second, third and fourth tensor bands. The first and second tensor bands are disposed in a crosswise fashion along the front body portion in a manner intended to substantially correspond to the front functional line extending along the upper body of the wearer. The third and fourth tensor bands are disposed in a crosswise fashion along the rear body portion in a manner intended to substantially correspond to the back functional line extending along the upper body of the wearer. Additionally, the orthopedic garment comprises fifth and sixth tensor bands. The fifth tensor band is laid out along the right sleeve portion in a manner intended to correspond to one of the fascial arm lines extending along the wearer's right arm. The sixth tensor band is laid out along the left sleeve portion in a manner intended to correspond to one of the fascial arm lines extending along the wearer's left arm.

In a further feature, the one fascial arm line extending along the wearer's right arm is selected from the group consisting of: (a) the superficial front arm line; (b) the deep front arm line; (c) the superficial rear arm line; and (d) the deep rear arm line. The one fascial arm line extending along the wearer's left arm is selected from the group consisting of: (a) the superficial front arm line; (b) the deep front arm line; (c) the superficial rear arm line; and (d) the deep rear arm line.

In still another feature, the orthopedic garment comprises fifth and sixth tensor bands. The fifth tensor band is laid out along the right sleeve portion in a manner intended to correspond to the superficial front arm line extending along the wearer's right arm. The sixth tensor band is laid out along the left sleeve portion in a manner intended to correspond to the superficial front arm line extending along the wearer's left arm.

In a different feature, the orthopedic garment of claim 18 further comprises fifth and sixth tensor bands. The fifth tensor band is laid out along the right sleeve portion in a manner intended to correspond to the superficial rear arm line extending along the wearer's right arm. The sixth tensor band is laid out along the left sleeve portion in a manner intended to correspond to the superficial rear arm line extending along the wearer's left arm.

In yet another feature, the orthopedic garment further comprises fifth, sixth, seventh and eighth tensor bands. The fifth tensor band is laid out along the right sleeve portion in a manner intended to correspond to the superficial front arm line extending along the wearer's right arm. The sixth tensor band is laid out along the left sleeve portion in a manner intended to correspond to the superficial front arm line extending along the wearer's left arm. The seventh tensor band is laid out along the right sleeve portion in a manner intended to correspond to the superficial rear arm line extending along the wearer's right arm. The eighth tensor band is laid out along the left sleeve portion in a manner intended to correspond to the superficial rear arm line extending along the wearer's left arm. Additionally, the first, second, third, fourth, fifth, sixth, seventh and eighth tensor bands are made of a first stretchable material and the remainder of the garment body is made of at least one stretchable material different than the first stretchable material. The first stretchable material is stiffer than the at least one stretchable material used to make the remainder of the garment body.

In a further feature, the left sleeve portion includes a first sleeve body, and a first shoulder part disposed at the upper end of the first sleeve body and nestled between each of the front and rear body portions. The first shoulder part including at least one shoulder tensor band laid out in a manner intended to substantially correspond to a portion of the wearer's left deltoid. The right sleeve portion includes a second sleeve body, and a second shoulder part disposed at the upper end of the second sleeve body and nestled between each of the front and rear body portions. The second shoulder part includes at least one shoulder tensor band laid out in a manner intended to substantially correspond to a portion of the wearer's right deltoid.

In an additional feature, the at least one shoulder tensor band of the first shoulder part includes first and second shoulder tensor bands. The first shoulder tensor band is laid out in a manner intended to substantially correspond to the muscle fibers of the wearer's front left deltoid. The second shoulder tensor band is laid out in a manner intended to substantially correspond to the muscle fibers of the wearer's rear left deltoid. The at least one shoulder tensor band of the second shoulder part includes third and fourth shoulder tensor bands. The third shoulder tensor band is laid out in a manner intended to substantially correspond to the muscle fibers of the wearer's front right deltoid. The fourth shoulder tensor band is laid out in a manner intended to substantially correspond to the muscle fibers of the wearer's rear right deltoid.

In still another feature, the first and second shoulder tensor bands meet at a point intended to substantially correspond to the deltoid tuberosity of the wearer's left arm. The third and fourth shoulder tensor bands meet at a point intended to substantially correspond to the deltoid tuberosity of the wearer's right arm. Additionally, the left sleeve portion includes a first circumferential band into which the first and second shoulder tensor bands converge and the right sleeve portion includes a second circumferential band into which the third and fourth shoulder tensor bands converge.

In a different feature, the left sleeve portion includes a first sleeve body terminating in a first cuff portion, and a first shoulder part disposed at the upper end of the first sleeve body and nestled between each of the front and rear body portions. The fifth tensor band is disposed on the first sleeve body between the upper end thereof and the first cuff portion. The right sleeve portion includes a second sleeve body terminating in a second cuff portion, and a second shoulder part disposed at the upper end of the second sleeve body and nestled between each of the front and rear body portions. The sixth tensor band is disposed on the second sleeve body between the upper end thereof and the second cuff portion.

In a further feature, the at least one tensor band is made of a first stretchable material and the remainder of the garment body is made of at least one stretchable material different than the first stretchable material. The first stretchable material is stiffer than the at least one stretchable material used to make the remainder of the garment body.

In an alternate feature, the garment body has a configuration selected from the group consisting of: (a) a long-sleeved shirt; (b) a t-shirt, (c) a bodysuit; and (d) a jumpsuit.

BRIEF DESCRIPTION OF THE DRAWINGS

The embodiments of the present invention shall be more clearly understood with reference to the following detailed description of the embodiments of the invention taken in conjunction with the accompanying drawings, in which:

FIG. 16 is a rear perspective view of the wearer and the orthopedic support garment illustrated in FIG. 2 showing the wearer's right arm fully extended in the release phase position which follows a baseball pitcher's throw.

DETAILED DESCRIPTION OF EMBODIMENTS OF THE INVENTION

Figure 1A:
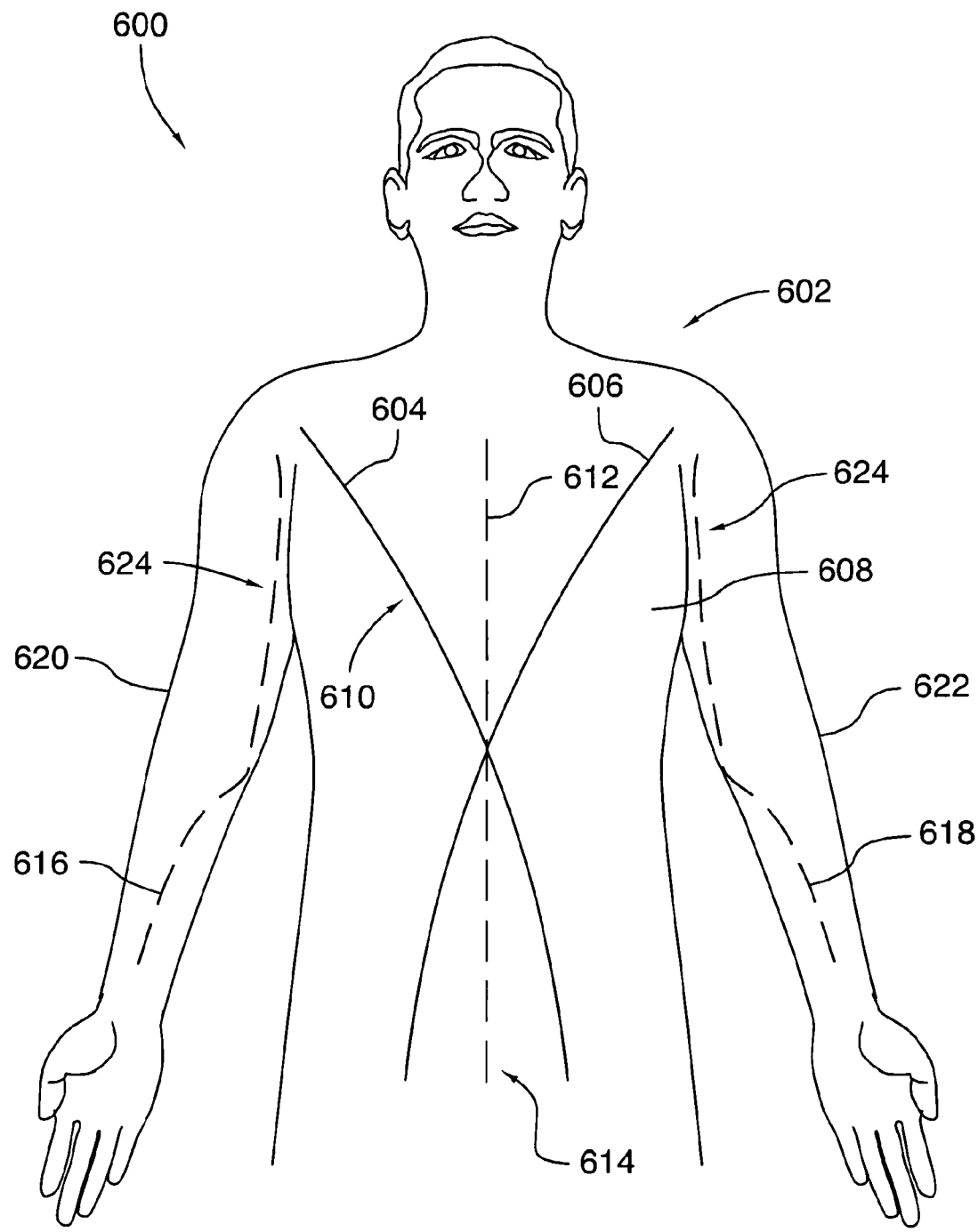
FIG. 1a is a schematic front end view of the upper body portion of a human body showing the arrangement of the superficial front arm lines, the front functional line and the front superficial line along the upper body portion.

The description, which follows, and the embodiments described therein are provided by way of illustration of an example, or examples of particular embodiments of principles and aspects of the present invention. These examples are provided for the purposes of explanation and not of limitation, of those principles of the invention. In the description that follows, like parts are marked throughout the specification and the drawings with the same respective reference numerals.

In the following description, the terms "left" and "right" are used with reference to a wearer of the orthopedic support garment as described and shown herein. Accordingly, the term "left" relates to elements that would be positioned towards or on the left side of the wearer's body if the wearer were wearing the orthopedic support garment, while the term "right" relates to elements that would be positioned towards or on the right side of the wearer's body, if the wearer were wearing the orthopedic support garment.

Moreover, the term "medial" is be used to refer to a direction pointing towards the center of the wearer's body, if the wearer were wearing the orthopedic support garment, while the term "lateral" is used to refer to a direction pointing away from the center of the wearer's body, if the wearer were wearing the orthopedic support garment, either toward the left or right side of the wearer's body.

Referring to FIGS. 2 to 8, there is an orthopedic support garment designated generally with reference numeral 10, shown being worn by a wearer 12. The garment 10 is intended to be worn tight-fitting or form-fitting on the upper part of a wearer's body. Advantageously, the garment 10 is configured to provide at least some resistance to movement of the wearer's upper body for enhanced support and injury prevention, and for fostering increased proprioception in the wearer 12. But, in contrast to conventional upper body compression or support garments, the support and resistance afforded by the garment 10 is directed at least in part along some of the fascial planes or lines running through the wearer's upper body.

By way of background, fascias are bands of fibrous connective tissue that lie below the skin in broad continuous planes in the body. Fascia envelops, separates or binds together muscles, organs and other soft structures of the body and provides support and protection to such body structures. Fascia works as a communication system between the tissues that are responsible for movement, including bone, joint structures (capsules, ligaments), and muscle/tendon units.

Figure 1B:
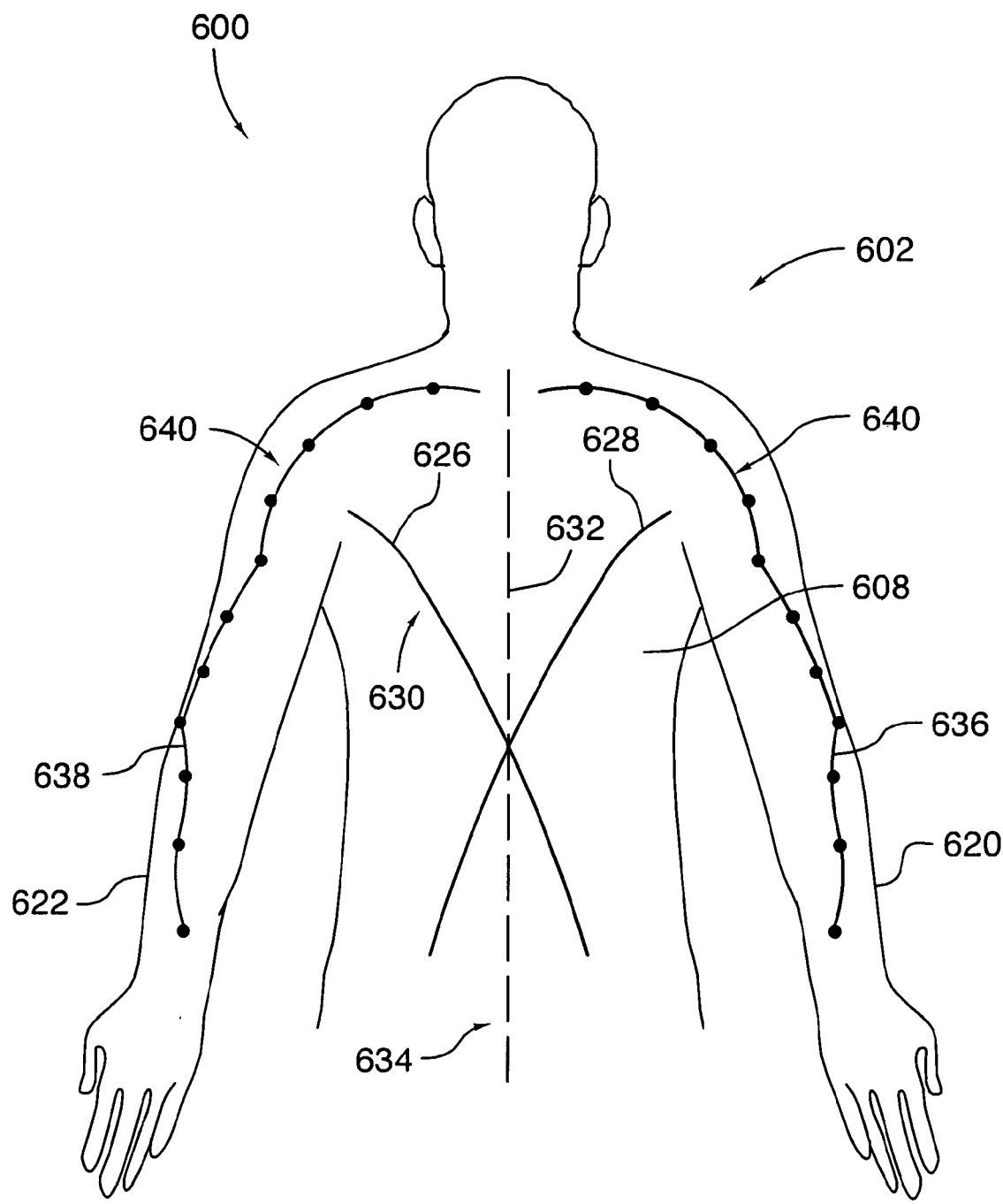
FIG. 1b is a schematic rear end view of the upper body portion of a human body showing the arrangement of the superficial rear arm lines, the back functional line and the back superficial line along the upper body portion.

Fascia can be seen to extend along meridians, planes or lines. FIGS. 1A and 1B show some of the fascial planes or lines running along the upper body portion 600 of a human body 602. In FIG. 1A, the diagonally intersecting lines 604 and 606 which extend along the torso 608 correspond to the front functional line 610; the vertical line 612 extending along the medial portion of the torso 608 corresponds to the superficial front line 614; and the lines 616 and 618 extending along the inside of the right and left arms 620 and 622, respectively, correspond to the superficial front arm lines 624.

In FIG. 1B, the diagonally intersecting lines 626 and 628 which extend along the torso 608 correspond to the back functional line 630; the vertical line 632 extending medially along the torso 608 corresponds to the superficial back line 634; and the lines 636 and 638 extending along the outside of the right and left arms 620 and 622, respectively, correspond to the superficial rear arm lines 640.

The lines of fascia described above are engaged during specific movement patterns. Imbalances within the fascia can lead to improper activation of muscles, which can ultimately predispose an individual to injury. By providing localized resistance (i.e. tension) along the fascial planes or lines (also known as myofascial meridians) of the wearer's upper body, the garment 10 recruits the neuromusculoskeletal fascial network to enhance proprioceptive (and kinesthetic) response. More specifically, the pressure applied by the shirt along the fascial anatomical planes tends to play a significant role, by enhancing proper muscle firing patterns during complex movements such as throwing a ball, serving in tennis, swinging a golf club to name a few. In this way, the garment can be used to facilitate an individual's kinesthetic sense, or knowledge of where their body is positioned in space during movement which can be very beneficial in improving athletic performance, rehabilitation from injury or preventing injury.

In this embodiment, the garment 10 takes the shape of a long-sleeved shirt 24. The shirt 24 has a body made up of front and rear body portions 28 and 30 joined to each other along left and right vertically extending seams (not shown) and right and left sleeve portions 36 and 38 attached to the front and rear body portions 28 and 30.

Figure 9:
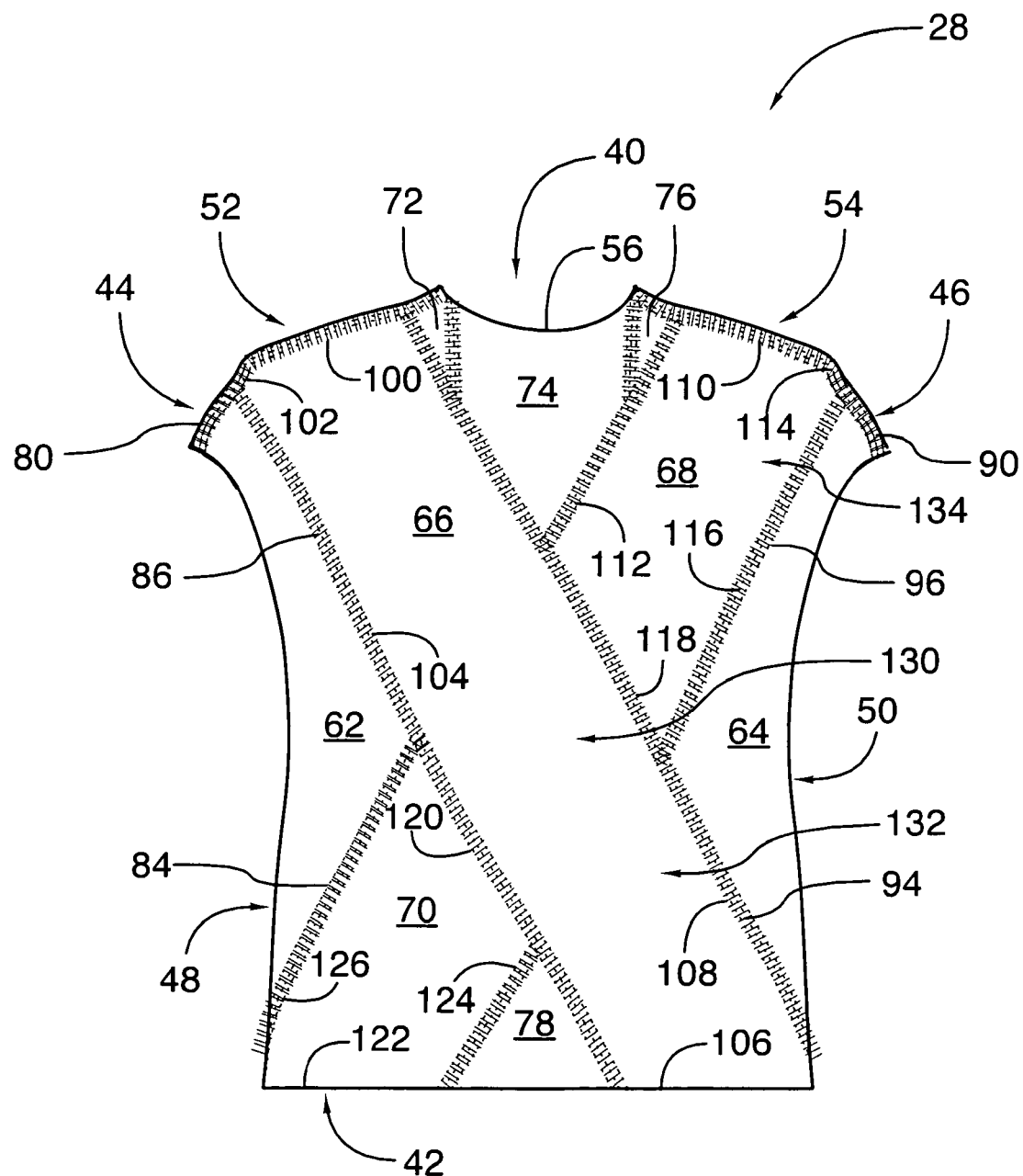
FIG. 9 is a front elevation view of the front body portion shown in FIG. 3.

As best shown in FIG. 9, the boundaries or margins of the front body portion 28 are defined by an upper edge 40; a lower edge 42; a pair of opposed, relatively short, right and left upper lateral edges 44 and 46; and a pair of opposed, relatively long, right and left lower lateral edges 48 and 50. The edge 48 is joined to like edge 168 of the rear body portion 30 to form the left vertically extending seam. Similarly, the edge 50 attached to like edge 170 of the rear body portion 30 to form the right vertically extending seam. The edges 48 and 50 extend substantially upwardly from the lower edge 42 to meet the right and left upper lateral edges 44 and 46, respectively. In turn, the edges 44 and 46 connect to the upper edge 40.

Figure 2:
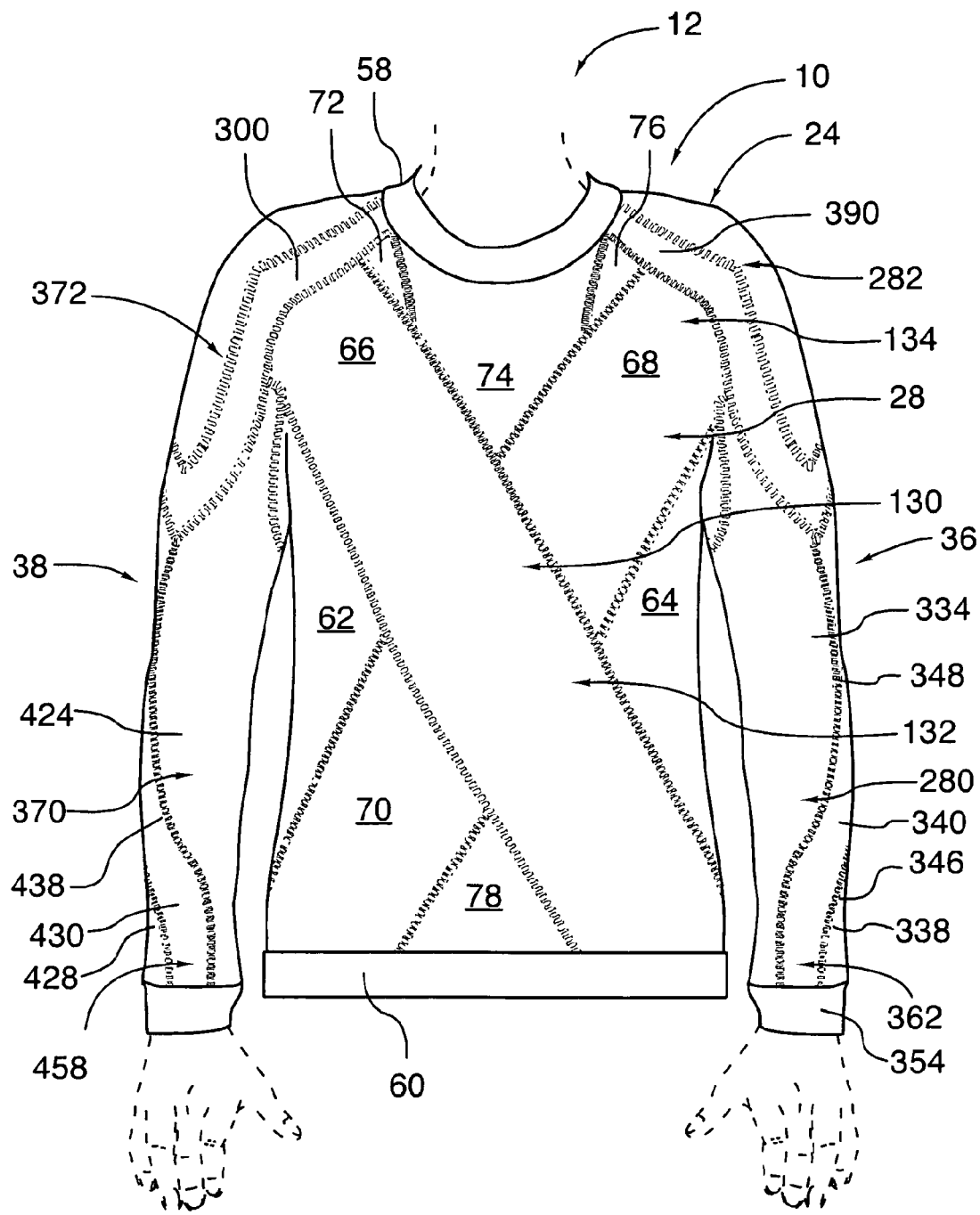
FIG. 2 is a front elevation view of an orthopedic support garment in accordance with an embodiment of the present invention shown being worn by a wearer.

The upper edge 40 includes a right upper edge portion 52, a left upper edge portion 54 and an intermediate upper edge portion 56 disposed between the right and left upper edge portions 52 and 54. The intermediate upper edge portion 56 has a downwardly concave shape that conforms to a correspondingly convex shape of collar portion 58. As shown in FIG. 2, the collar portion 58 is attached to the front body portion 28 along the intermediate upper edge portion 56.

The right upper edge portion 52 runs diagonally downward away from the intermediate upper edge portions 56 to meet the right upper lateral edge 44. On the opposite side, the left upper edge portion 54 is disposed in a mirror image to the right upper edge portion 52. The edge portion 54 extends diagonally downward from the intermediate upper edge portion 56 to join the left upper lateral edge 46.

In contrast to the upper edge 40, the lower edge 42 runs substantially straight from the right lateral lower edge 48 to the left lateral lower edge 50. As shown in FIG. 2, the waistband portion 60 is attached to the front body portion 28 along the lower edge 42.

The front body portion 28 can be seen to be formed by a plurality of fabric panels assembled to each other. In this embodiment, the front body portion 28 is made up of nine (9) panels stitched together—a right lateral panel 62; a left lateral panel 64; first, second and third diagonally-extending panels 66, 68 and 70; first second and third upper medial panels 72, 74 and 76; and a lower panel 78. It will be appreciated that, in other embodiments, the front body portion of the orthopedic support garment could be made with a greater or lesser number of panels.

Each of the panels 62, 64, 66, 68, 70, 72, 74, 76 and 78 will now be described in greater detail with reference to FIGS. 2, 3 and 9. The right lateral panel 62 vaguely resembles a triangle with two truncated corners. The boundaries or margins of the panel 62 are defined by the lower part 80 of the right upper lateral edge 44, the right lower lateral edge 48, a lower medial edge 84 and an upper medial edge 86. The lower part 80 of the right upper lateral edge 44 runs diagonally downward to join to the right lower lateral edge 48. The edge 48 extends downwardly toward the waistband portion 60 until it meets the lower medial edge 84. The edge 84 extends diagonally in a medial direction to meet the upper medial edge 86. Lastly, the edge 86 runs diagonally in a lateral direction to join the lower part 80 of the right upper lateral edge 44.

The left lateral panel 64 has substantially the same shape as the right lateral panel 62—it too vaguely resembles a triangle with two truncated corners. The panel 64 is arranged to be the mirror image of the panel 62. In the case of the left lateral panel 64 its boundaries are defined by the lower part 90 of the left upper lateral edge 46, the left lower lateral edge 50, a lower medial edge 94 and an upper medial edge 96. The lower part 90 of the left upper lateral edge 44 runs diagonally downward to join to the left lower lateral edge 50. The edge 50 extends downwardly toward the waistband portion 60 until it meets the lower medial edge 94. The edge 94 extends diagonally in a medial direction to meet the upper medial edge 96. Lastly, the edge 96 runs diagonally in a lateral direction to join the lower part 90 of the left upper lateral edge 46.

The first diagonally-extending panel 66 is shaped to vaguely resemble a rectangle with one of its corners truncated. The margins of the panel 66 are defined by the lower part 100 of the right upper edge portion 52, a relatively short upper lateral edge 102, a relatively long lower lateral edge 104, the part 106 of the lower edge 42, and a relatively long medial edge 108 disposed substantially parallel to the lower lateral edge 104. The panel 66 extends diagonally from right to left from the upper edge 40 to the lower edge 42 in effect tying the right sleeve portion 38 to the waistband portion 60. Along its lower lateral edge 104, the panel 66 is attached to the right lateral panel 62, the third diagonally-extending panel 70 and the lower panel 78. Along its medial edge 108, the panel 66 is joined to the left lateral panel 64, the second diagonally-extending panel 68 and the first and second upper medial panels 72 and 74.

The second diagonally-extending panel 68 is similar to panel 66 in that it too has a shape that is vaguely similar to that of a rectangle with one of its corners truncated. However, panel 68 is relatively shorter than panel 66. Delimiting the boundaries of the panel 68 are the lower part 110 of the left upper edge portion 54, a medial edge 112, a relatively short upper lateral edge 114, a relatively long lateral edge 116 and a lower edge 118. The panel 68 is disposed in the upper left region of the front panel portion 28 and attaches the left sleeve portion 36 to the panel 66. The panel 68 is bounded on one side by the second and third medial panels 74 and 76 and on the other side by the left lateral panel 64.

The third diagonally-extending panel 70 has a generally frusto-conical shape defined by an upper edge 120, a lower edge 122, a relatively short medial edge 124 and a relatively long lateral edge 126 disposed substantially parallel to medial edge 124. The panel 70 is disposed in the lower right region of the front panel portion 28 and attaches the first diagonally-extending panel 66 to the waistband portion 60, and the right lateral panel 62 to the lower panel 78.

The first, second and third diagonally-extending panels 66, 68 and 70 co-operate with each other to define an X-shaped or cross-like structure 130 extending across the front panel portion 28. The first panel 66 defines a first arm 132 of the cross-like structure 130, while the second and third panel 68 and 70 together define the second arm 134 of the structure 130. The arms 132 and 134 are disposed on the front panel portion 28 in a manner intended to substantially correspond to, follow, or trace, the diagonal fascial lines 604 and 606 that run along the front of the wearer's upper body and define the front functional line 610 (see FIG. 1A). Having the arms 132 and 134 disposed in this manner provides at least some tension and resistance to movement along the diagonal fascial planes thereby affording enhanced anatomically appropriate orthopedic support and proprioceptive (and kinesthetic) feedback to the wearer 12. Each arm 132, 134 is capable of functioning as a front diagonal tensor band, stretching (and providing resistance), when engaged by the wearer's movement.

In this embodiment, the arms 132 and 134 of the cross-like structure have straight edges. In other embodiments, the edges of the arms could be configured differently. For instance, they could be zig-zagging, ondulated or the like.

The orthopedic support garment 10 shown in FIG. 2 is specifically designed to be worn by a right-handed person as the first diagonally-extending panel 66 extends continuously and uninterruptedly between the right sleeve portion 38 and the waistband portion 60 for superior support. However, it will be appreciated that with proper modification the orthodontic support garment could be configured for a left-handed person. In such case, the arrangement of first, second and third diagonally-extending panels in the front body portion of such a garment would be the mirror image of that shown in FIG. 2. More specifically, there would be a continuous and an uninterruptedly diagonally-extending panel running from the left sleeve portion to the waistband portion. Modifications would also be required to be made to the position and orientation of the diagonally-extending panels of the rear body portion; these are described in greater detail below.

Figure 11A:
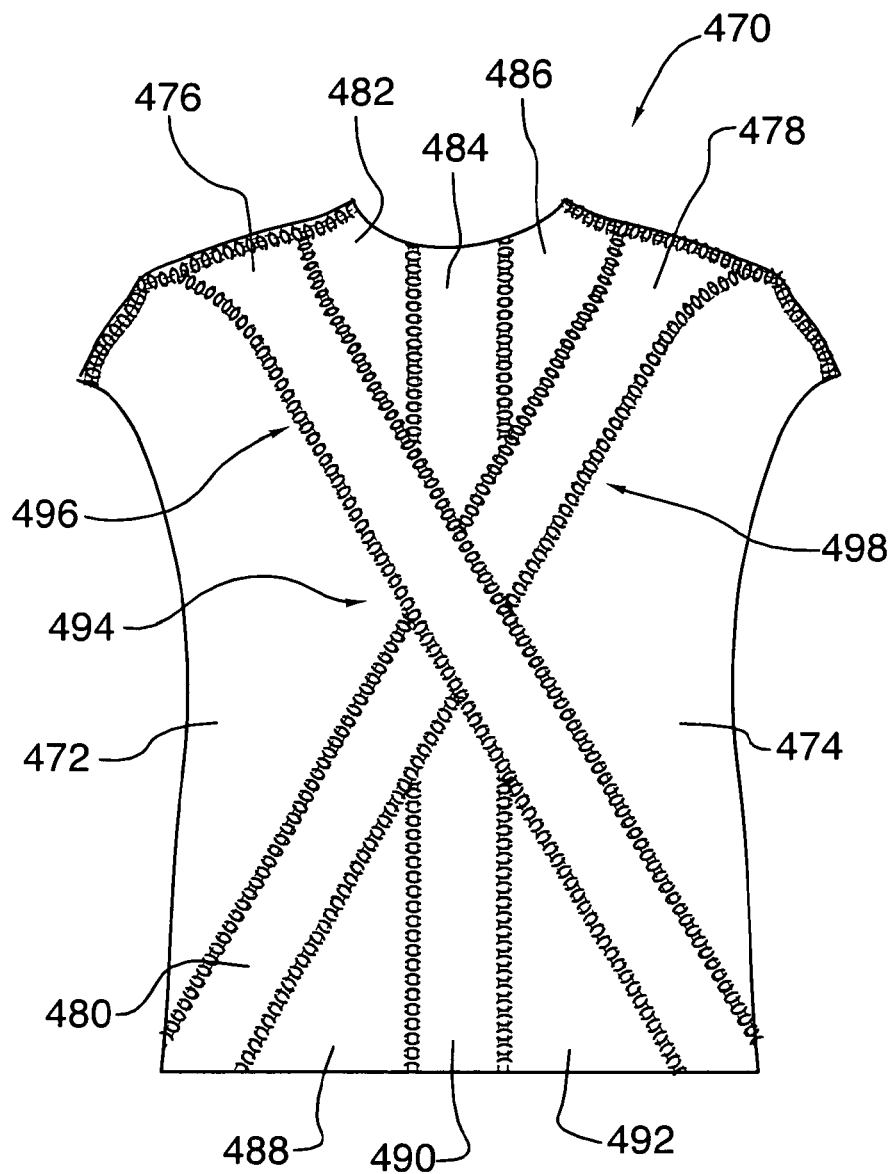
FIG. 11A is a front elevation view of a first alternate front body panel to that shown in FIG. 9.
Figure 11B:
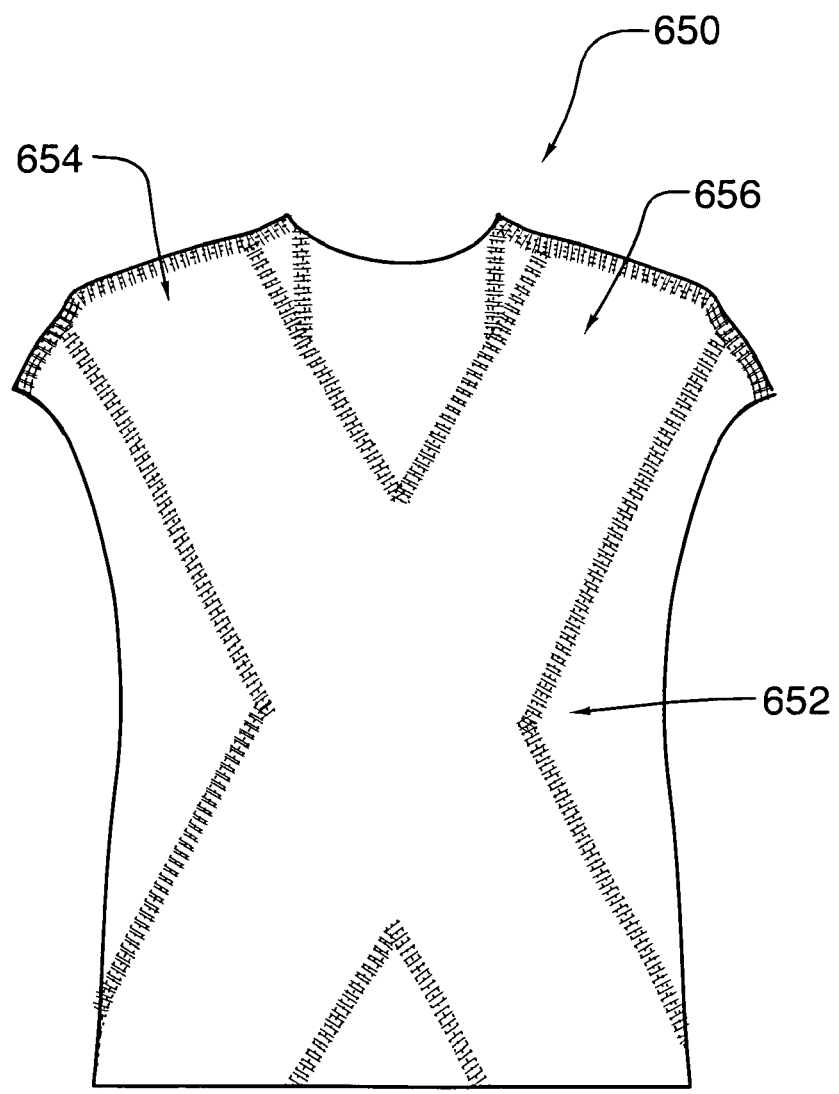
FIG. 11B is a front elevation view of a second alternate front body panel to that shown in FIG. 9.

A person skilled in the art will appreciate that additional modifications could be brought to the cross-like structure 130. In the embodiment shown in FIG. 2, the arms 132 and 134 of the cross-like structure 130 are arranged in a non-overlapping fashion made possible by the fact that the arm 134 is built up of two panels that are connected to each other only via the arm 132. This need not be the case in every application. In an alternative embodiment, it may be possible to fabricate each arm of the cross-like structure from a single panel of fabric and arrange such panels in an overlapping fashion such that one panel partially overlies the other panel when forming the cross-like structure. In still another embodiment, the cross-like structure could be made of a single fabric panel. Such an embodiment is illustrated in FIG. 11B wherein an alternative front body portion 650 is provided with a cross-like structure 652 having two diagonally extending panels 654 and 656 integrally formed with each other from a single fabric panel.

Moreover, while in the embodiment shown in FIG. 2, each panel 66, 68 and 70 is made up of a single piece of fabric, in alternative embodiments, it may be possible to fabricate one or more panels from a plurality of elongate fabric strips disposed side-by-each and stitched together. In such embodiments, the strips could be made of the same fabric material or could be made of different materials having different elasticity characteristics for variable resistance or stiffness along a particular line or plane.

Lastly, while it is generally preferred that the front panel portion be provided with two arms arranged in a cross-like structure that function as tensors bands, in certain special applications, it may be desirable to have only a single diagonally-extending panel which connects only one of the sleeve portions to the waistband.

Turning now to the first second and third upper medial panels 72, 74 and 76, the first and third panels 72 and 76 are relatively small panels and are similar to each other in that each has a triangular shape. The first are third panels 72 and 76 are disposed on either side of the second panel 74 in a mirror image arrangement. The panel 72 serves to reinforce the connection between the right sleeve portion 38 and the first diagonally-extending panel 66. Similarly, the panel 76 reinforces the connection between the left sleeve portion 36 and the second diagonally-extending panel 68 and act as stabilizers of the back fascial lines.

The second upper medial panel 74 is intended to be oriented along the superficial front line 614 when the garment 10 is worn by the wearer 12. The panel 74 has a wedge-like shape and is nestled between the first and second upper medial panels 72 and 76, the first and second diagonally-extending panels 66 and 68, and the collar portion 58. The intermediate upper edge portion 56 to which is secured the collar portion 58, defines the uppermost margin of the panel 74.

Lastly, the lower panel 78 has a triangular shape and is positioned between the first and third diagonally-extending panels 66 and 70 and the waistband portion 60. Like the second upper medial panel portion 74, the lower panel 78 is intended to be oriented along the superficial front line 614 when the garment 10 is worn by the wearer.

In this embodiment, the panels 66, 68, 70, 72, 74, 76 and 78 of the front body portion 28 are sewn together along several seams, namely: first and second, relatively long, diagonal seams 140 and 142; first, second, third and fourth, relatively short, diagonal seams 144, 146, 148 and 150; and first and second, relatively short, vertical seams 152 and 154. The lower lateral edge 104 of the panel 66 is attached to the upper medial edge 96 of the right lateral panel 62, the upper edge 110 of the panel 70 and the lower portion 78 along the first long diagonal seam 140. The medial edge 108 of the panel 66 is joined to the first and second upper medial panels 72 and 74, the lower edge 118 of the panel 68, and the lower medial edge 84 of the left lateral panel 64 along the second long diagonal seam 142.

The first short diagonal seam 144 connects the medial edge 112 of the panel 68 to the panels 72 and 74. The second short diagonal seam 146 joins the lateral edge 116 of the panel 68 to the upper medial edge 86 of the left side panel 64. The long lateral edge 126 of the panel 70 is attached to the lower medial edge 84 of the right side panel 62 along the third short diagonal seam 148, while the short medial edge 124 of the panel 70 is joined to the lower portion 78 along the fourth short diagonal seam 150. Lastly, the first short vertical seam 152 joins the panel 72 to the panel 74 and the second short vertical seam 154 connects the panel 74 to the panel 76.

In other embodiments, the number, orientation and location of the various seams could be different to match an alternate configuration of the front body portion.

In other embodiments, the front body portion could be configured differently, for instance, with a greater or lesser number of panels. FIG. 11A shows an alternate front panel portion designated generally with reference numeral 470 that is provided with additional panels for improved support and increased tensile resistance. The front panel portion 470 is generally similar to the front panel portion 28 shown in FIG. 10 in that it too is formed by a plurality of fabric panels assembled to each other. However, in contrast to the front body portion 28 which is made up of nine (9) panels, the front panel portion 470 is made up of eleven (11) panels (i.e. with two additional panels). The front panel portion 470 includes a right lateral panel 472; a left lateral panel 474; first, second and third diagonally-extending panels 476, 478 and 480; first second and third upper medial panels 482, 484 and 486; and first, second and third lower medial panels 488, 490 and 492.

The configuration and arrangement of the panels 472, 474, 476, 478 and 480 resemble that of counterpart panels 62, 64, 66, 68 and 70, except that diagonally-extending panels 476, 478 and 480 are formed with a narrower width than the diagonally extending panels 66, 68 and 70 and their upper ends flare out slightly. This is to accommodate the different arrangement of upper and lower medial panels 482, 484, 486, 488, 490 and 492.

The first, second and third upper medial panels 482, 484 and 486 are disposed between the first and second diagonally-extending panels 476 and 478. The panels 482, 484 and 486 are shaped differently than the panels 72, 74 and 76 of the front panel portion 28. More specifically, the first and third panels 482 and 486 are sized bigger than their counterpart panels 72 and 76, while the second panel 484 is sized smaller than the second panel 74. The first and third upper medial panels 482 and 486 are similar to each other in that each has a substantially triangular shape. The first and third panels 482 and 486 are disposed on either side of the second panel 484 in a mirror image arrangement. The second upper medial panel 484 has an elongated shape with a tapering end. The panel 484 is nestled between the first and second upper medial panels 482 and 486, the first and second diagonally-extending panels 476 and 478, and a collar portion (not shown).

The first, second and third lower medial panels 488, 490 and 492 are disposed between the first and third diagonally-extending panels 476 and 480. The first and third lower medial panels 488 and 492 are similar to each other in that each has a triangular shape. The first and third panels 488 and 492 are disposed on either side of the second panel 490 in a mirror image arrangement, and are bounded by the first and third diagonally-extending panels 476 and 480, respectively. The second lower medial panel 490 has an elongated shape with a tapering end. The panel 490 is nestled between the first and second lower medial panels 488 and 492, the first and third diagonally-extending panels 476 and 480, and a waistband portion (not shown).

Figure 10:
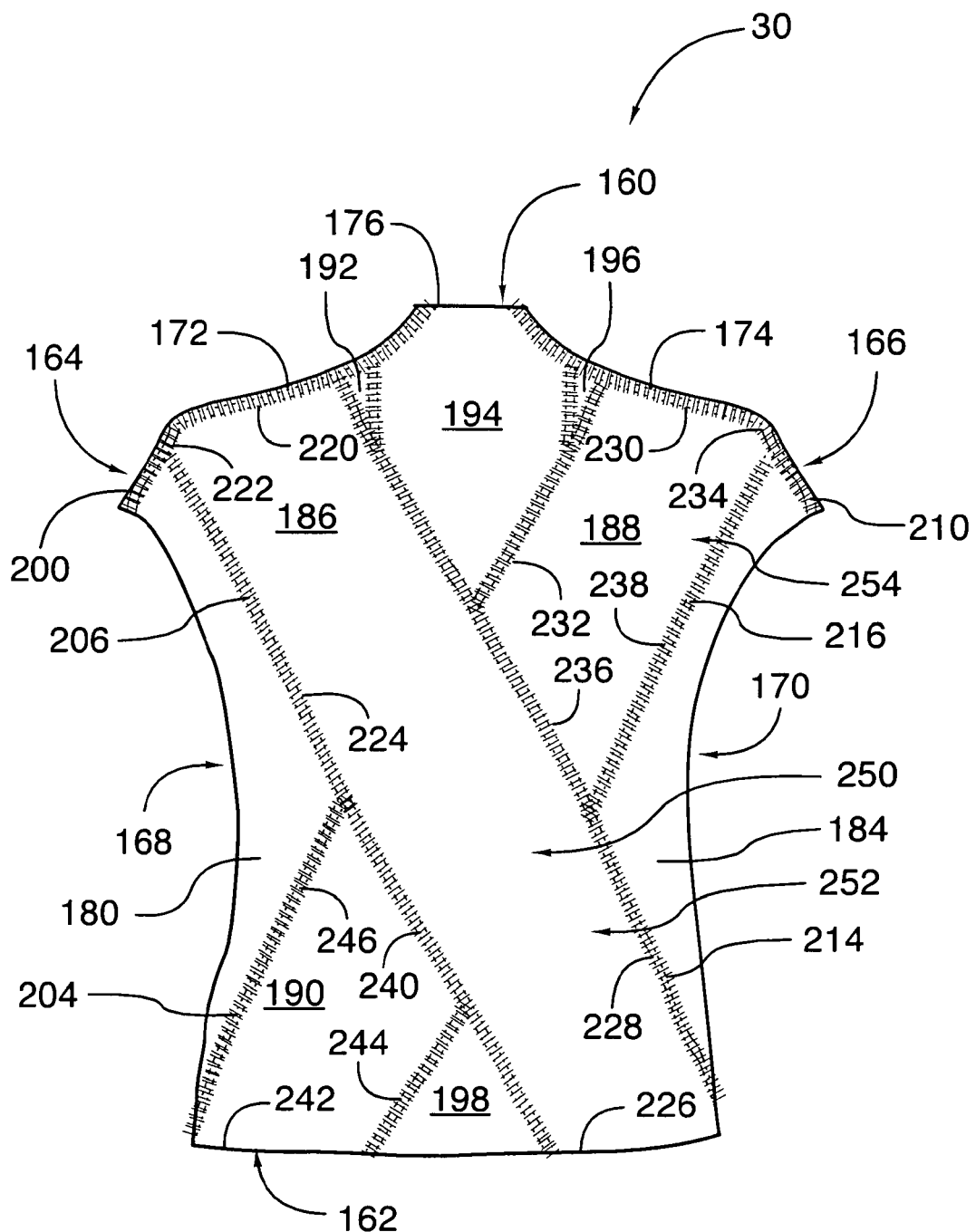
FIG. 10 is a front elevation view of the rear body portion shown in FIG. 4.

In this embodiment, the first, second and third diagonally-extending panels 476, 478 and 480 co-operate with each other to define an X-shaped or cross-like structure 494 extending across the front panel portion 470 (not unlike, the cross-like structure 130 of front panel 28 shown in FIG. 10). The first panel 476 defines a first arm 496 of the cross-like structure 494, while the second and third panel 478 and 480 together define the second arm 498 of the structure 494. The arms 496 and 498 are disposed on the front panel portion 470 in a manner intended to substantially correspond to, follow, or trace, the diagonal fascial lines 604 and 606 that run along the front of the wearer's upper body and define the front functional line 610 (see FIG. 1A). Each arm 496, 498 is capable of functioning as a front diagonal tensor band, stretching (and providing resistance), when engaged by the wearer's movement.

However, in addition to having front diagonal tensors bands defined by arms 486 and 498 of the cross-like structure 494, the front panel portion 470 also has a front vertical tensor band defined cooperatively by the second upper medial panel 484 and the second lower medial panel 490. This vertical tensor band is disposed on the front panel portion 470 in a manner intended to substantially correspond to, follow, or trace, the center fascial line 612 that runs along the front of the wearer's upper body and defines the superficial front line 614 (see FIG. 1A). The vertical tensor band can be engaged when the wearer extends his/her trunk.

Figure 4:
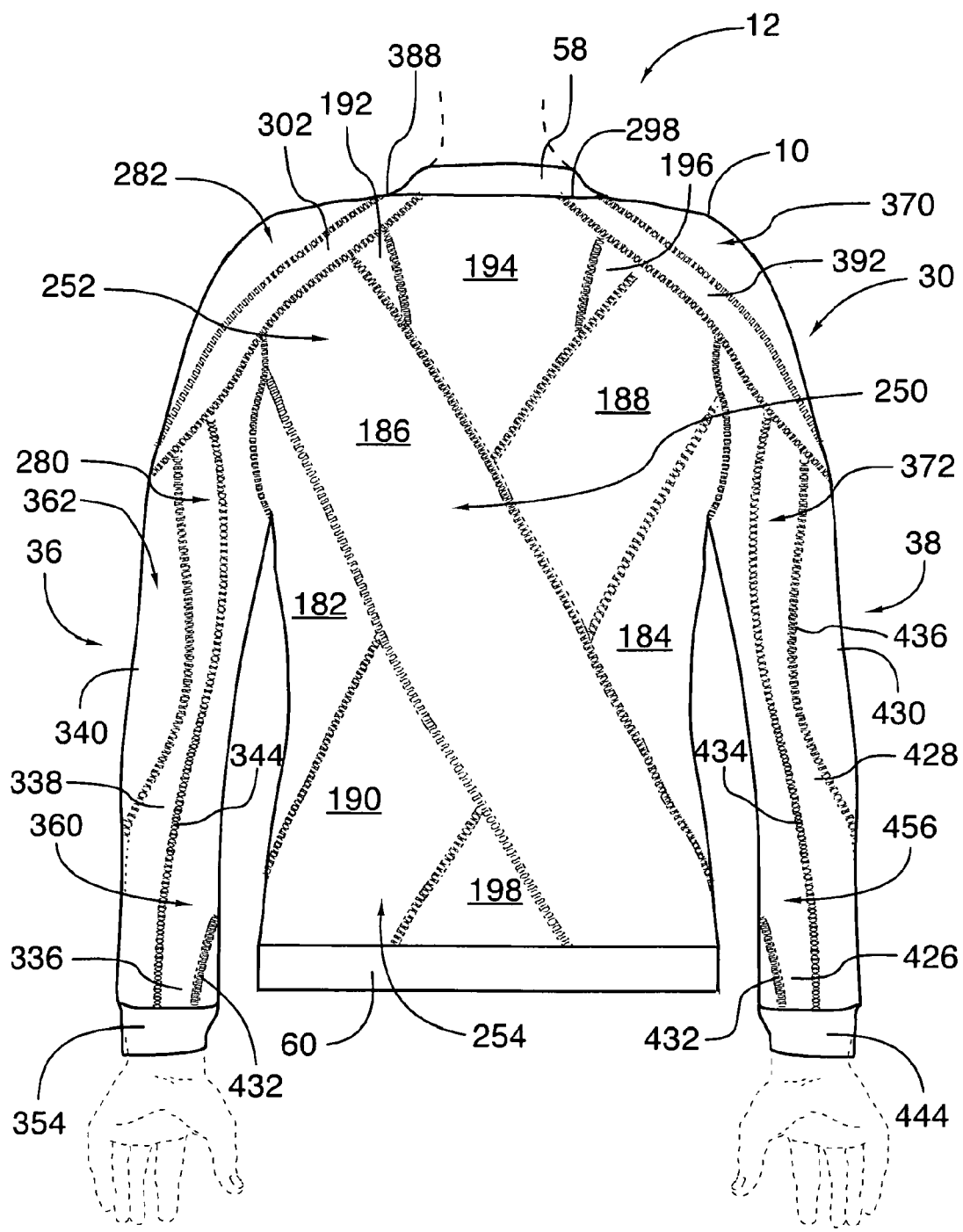
FIG. 4 is a rear elevation view of the wearer and the orthopedic support garment shown in FIG. 2.

The rear body portion 32 will now be described in greater detail with reference to FIGS. 4, 5 and 10. The boundaries or margins of the rear body portion 30 are defined by an upper edge 160; a lower edge 162; a pair of opposed, relatively short, left and right upper lateral edges 164 and 166; and a pair of opposed, relatively long, left and right lower lateral edges 168 and 170. The edges 168 and 170 extend substantially upwardly from the lower edge 162 to meet the left and right upper lateral edges 164 and 166, respectively. In turn, the edges 164 and 166 connect to the upper edge 160.

The upper edge 160 includes a left upper edge portion 172, a right upper edge portion 174 and an intermediate upper edge portion 176 disposed between the left and right upper edge portions 172 and 174. As shown in FIG. 4, the collar portion 58 is attached to the rear body portion 30 along the intermediate upper edge portion 176.

The left upper edge portion 172 curved slightly concavely and runs downwardly from the intermediate upper edge portions 176 to meet the left upper lateral edge 164. On the opposite side, the right upper edge portion 174 is disposed in a mirror image to the left upper lateral edge portion 172. The edge portion 174 extends downwardly from the intermediate upper edge portion 176 to join the right upper lateral edge 166.

In contrast to the upper edge 160, the lower edge 162 runs substantially straight from the left lateral lower edge 168 to the right lateral lower edge 170. As shown in FIG. 4, the waistband portion 60 is attached to the rear body portion 30 along the lower edge 162.

The rear body portion 30 is generally similar to the front body portion 28 in that it too is formed from a plurality of fabric panels assembled to each other. In this embodiment, the rear body portion 30 is made up of nine (9) panels stitched together—a left lateral panel 182; a right lateral panel 184; first, second and third diagonally-extending panels 186, 188 and 190; first second and third upper medial panels 192, 194 and 196; and a lower panel 198. It will be appreciated that, in other embodiments, the rear body portion of the orthopedic support garment could be made with a greater or lesser number of panels.

Each of the panels 182, 184, 186, 188, 190, 192, 194, 196 and 198 will now be described in greater detail with reference to FIGS. 4, 5 and 10. The left lateral panel 182 is substantially similar to the left lateral panel 62 of the front body portion 28 described above. The panel 182 has boundaries or margins that are defined by the lower part 200 of the left upper lateral edge 164, the left lower lateral edge 168, a lower medial edge 204 and an upper medial edge 206. The lower part 200 of the left upper lateral edge 164 runs diagonally downward to join to the left lower lateral edge 168. The edge 168 extends downwardly toward the waistband portion 60 until it meets the lower medial edge 204. The edge 204 extends diagonally in a medial direction to meet the upper medial edge 206. Lastly, the edge 206 runs diagonally in a lateral direction to join the lower part 200 of the left upper lateral edge 164.

The right lateral panel 184 closely resembles the right lateral panel 64 of the front body portion 28. Its boundaries are defined by the lower part 210 of the right upper lateral edge 166, the right lower lateral edge 170, a lower medial edge 214 and an upper medial edge 216. The lower part 210 of the right upper lateral edge 164 runs diagonally downward to join to the right lower lateral edge 170. The edge 170 extends downwardly toward the waistband portion 60 until it meets the lower medial edge 214. The edge 214 extends diagonally in a medial direction to meet the upper medial edge 216. Lastly, the edge 216 runs diagonally in a lateral direction to join the lower part 210 of the right upper lateral edge 166.

The first diagonally-extending panel 186 has a shape very similar to that of the first diagonally-extending panel 66 of the front body portion 28, except that it somewhat shorter than panel 66. The margins of the panel 186 are defined by the lower part 220 of the left upper edge portion 172, a relatively short upper lateral edge 222, a relatively long lower lateral edge 224, the part 226 of the lower edge 162, and a relatively long medial edge 228 disposed substantially parallel to the lower lateral edge 124. In contrast to the first diagonally-extending panel 66 which extends from right to left from the upper edge 40 to the lower edge 42, the panel 186 extends from left to right from the upper edge 160 to the lower edge 162, tying the left sleeve portion 36 to the waistband portion 60. Along its lower lateral edge 224, the panel 186 is attached to the left lateral panel 182, the third diagonally-extending panel 190 and the lower panel 198. Along its medial edge 228, the panel 186 is joined to the right lateral panel 184, the second diagonally-extending panel 188 and the first and second upper medial panels 192 and 194.

The second diagonally-extending panel 188 is shaped similar to its counterpart panel 68 in the front body portion 28. The boundaries of the panel 188 are delimited by the lower part 230 of the right upper edge portion 174, a medial edge 232, a relatively short upper lateral edge 234, a relatively long lower lateral edge 236 and a lower edge 238. The panel 188 is disposed in the upper right region of the rear panel portion 30 and attaches the right sleeve portion 38 to the panel 186. The panel 188 is bounded on one side by the second and third medial panels 194 and 196 and on the other side by the right lateral panel 184.

The third diagonally-extending panel 190 is shaped to resemble panel 70 of the front body portion 28. It has an upper edge 240, a lower edge 242, a relatively short medial edge 244 and a relatively long lateral edge 246 disposed substantially parallel to medial edge 244. The panel 190 is disposed in the lower left region of the rear panel portion 30 and attaches the first diagonally-extending panel 186 to the waistband portion 60, and the left lateral panel 182 to the lower panel 198.

The first, second and third diagonally-extending panels 186, 188 and 190 co-operate with each other to define an X-shaped or cross-like structure 250 (not unlike cross-structure 130) extending across the rear panel portion 30. The first panel 186 defines a first arm 252 of the cross-like structure 250, while the second and third panel 188 and 190 together define the second arm 254 of the structure 250. The arms 252 and 254 are disposed on the rear panel portion 30 in a manner intended to substantially correspond to, follow, or trace, the diagonal fascial lines 626 and 628 (shown in FIG. 1B) that run along the rear of the wearer's upper body. As is the case with arms 132 and 134, having the arms 252 and 254 disposed in this manner provides at least some tension and resistance to movement along the diagonal fascial planes thereby affording enhanced anatomically appropriate orthopedic support and proprioceptive (and kinesthetic) feedback to the wearer 12. Each arm 252, 254 is capable of functioning as a rear diagonal tensor band, stretching (and providing resistance), when engaged by the wearer's movement.

As mentioned previously, the orthopedic support garment 10 is specifically designed to be worn by a right-handed person. However, it will be appreciated that with proper modification the orthodontic support garment could be configured for a left-handed person. In such case, the arrangement of first, second and third diagonally-extending panels in the rear body portion of such a garment would be the mirror image of that shown in FIG. 4. More specifically, there would be a continuous and an uninterrupted diagonally-extending panel running from the right sleeve portion to the waistband portion. Additionally, the position and orientation of the diagonally-extending panels of the front body portion would be modified as described above.

A person skilled in the art will appreciate that modifications similar to those described above in the context of the cross-like structure 130, could also be brought to the cross-like structure 250 such that there is no need to repeat the description thereof here. In addition, in other embodiments, the rear body portion could be configured differently, for instance, with a greater or lesser number of panels. In this regard, the rear panel portion could be made to resemble the alternate front panel portion shown in FIG. 11A or FIG. 11B.

Turning now to the first second and third upper medial panels 192, 194 and 196, these are generally similar to their counterpart panels 72, 74 and 76 of the front body portion 28. Like panels 72 and 76, the first and third panels 192 and 196 are relatively small triangular panels. The first are third panels 192 and 196 are disposed on either side of the second panel 194 in a mirror image arrangement. The panel 192 serves to reinforce the connection between the left sleeve portion 36 and the first diagonally-extending panel 186.

Similarly, the panel 196 reinforces the connection between the right sleeve portion 38 and the second diagonally-extending panel 188.

The second upper medial panel 194 is intended to be oriented along the superficial back line 634 (shown in FIG. 1B) when the garment 10 is worn by the wearer 12. The panel 194 is shaped similar to an arrowhead and is nestled between the first and second upper medial panels 192 and 196, the first and second diagonally-extending panels 186 and 188, and the collar portion 58. The intermediate upper edge portion 176 to which is secured the collar portion 58, defines the uppermost margin of the panel 194.

Lastly, the lower panel 198 has a triangular shape and is positioned between the first and third diagonally-extending panels 186 and 190 and the waistband portion 60. Like the second upper medial panel 194, the lower panel 198 is intended to be oriented along the superficial back line 634 when the garment 10 is worn by the wearer 12.

In this embodiment, the panels 186, 188, 190, 192, 194, 196 and 198 of the rear body portion 30 are sewn together along several seams, namely: first and second, relatively long, diagonal seams 260 and 262; first, second, third and fourth, relatively short, diagonal seams 264, 266, 268 and 270; and first and second, relatively short, vertical seams 272 and 274. The lower lateral edge 124 of the panel 186 is attached to the upper medial edge 106 of the left lateral panel 182, the upper edge 240 of the panel 190 and the lower portion 198 along the first long diagonal seam 260. The medial edge 128 of the panel 186 is joined to the first and second upper medial panels 192 and 194, the lower edge 238 of the panel 188, and the lower medial edge 214 of the right lateral panel 184 along the second long diagonal seam 262.

The first short diagonal seam 264 connects the medial edge 232 of the panel 188 to the panels 192 and 194. The second short diagonal seam 266 joins the lateral edge 236 of the panel 188 to the upper medial edge 216 of the right side panel 184. The long lateral edge 246 of the panel 190 is attached to the lower medial edge 104 of the left side panel 182 along the third short diagonal seam 268, while the short medial edge 244 of the panel 190 is joined to the lower portion 198 along the fourth short diagonal seam 270. Lastly, the first short vertical seam 272 joins the panel 192 to the panel 194 and the second short vertical seam 274 connects the panel 194 to the panel 196.

In other embodiments, the number, orientation and location of the various seams could be different to match an alternate configuration of the rear body portion.

Figure 5:
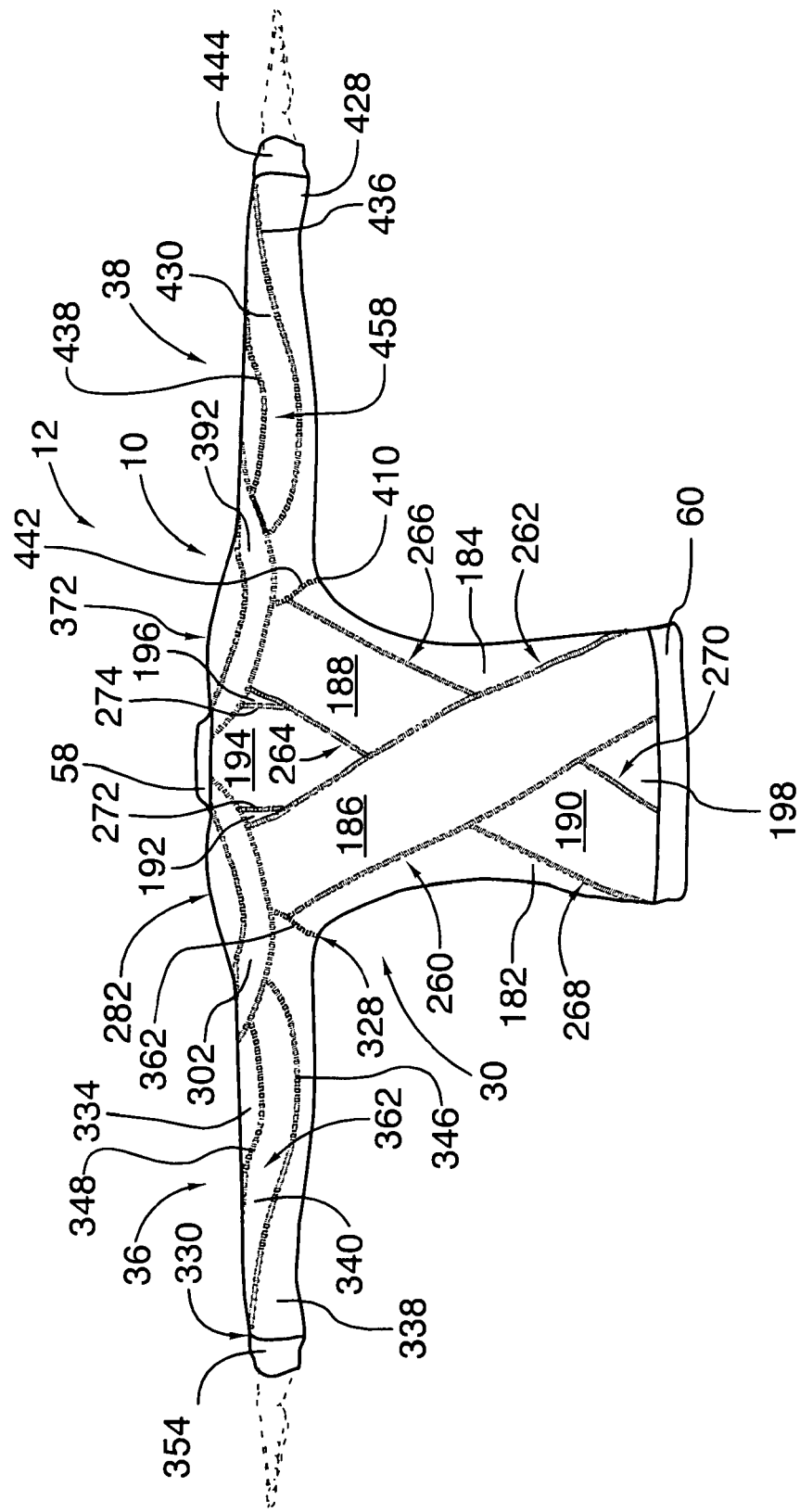
FIG. 5 is another rear elevation view of the wearer and the orthopedic support garment similar to that illustrated in FIG. 4, with the wearer's arms raised laterally away from their body.
Figure 6:
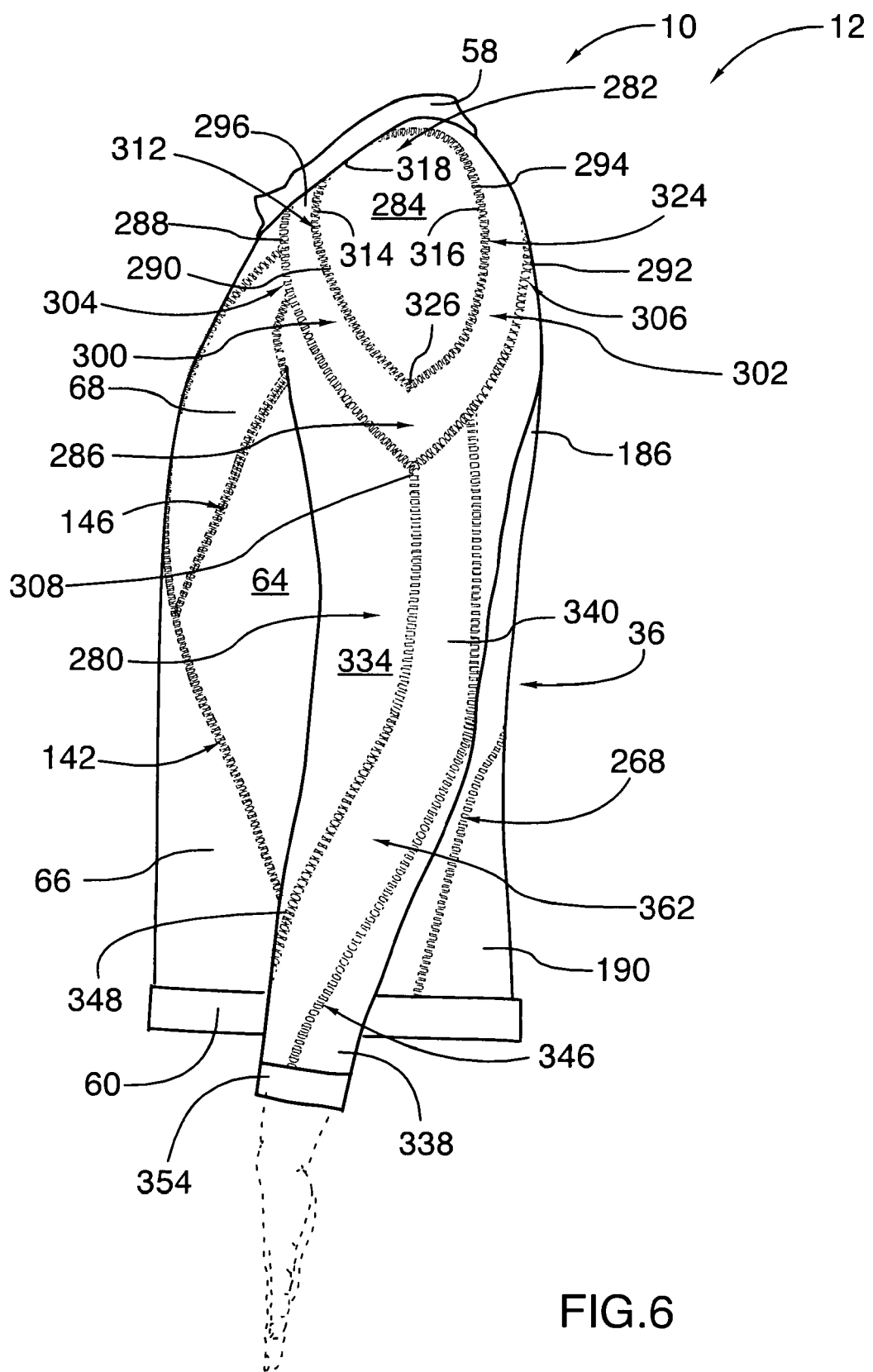
FIG. 6 is a left hand side elevation view of the wearer and the orthopedic support garment shown in FIG. 2.
Figure 7:
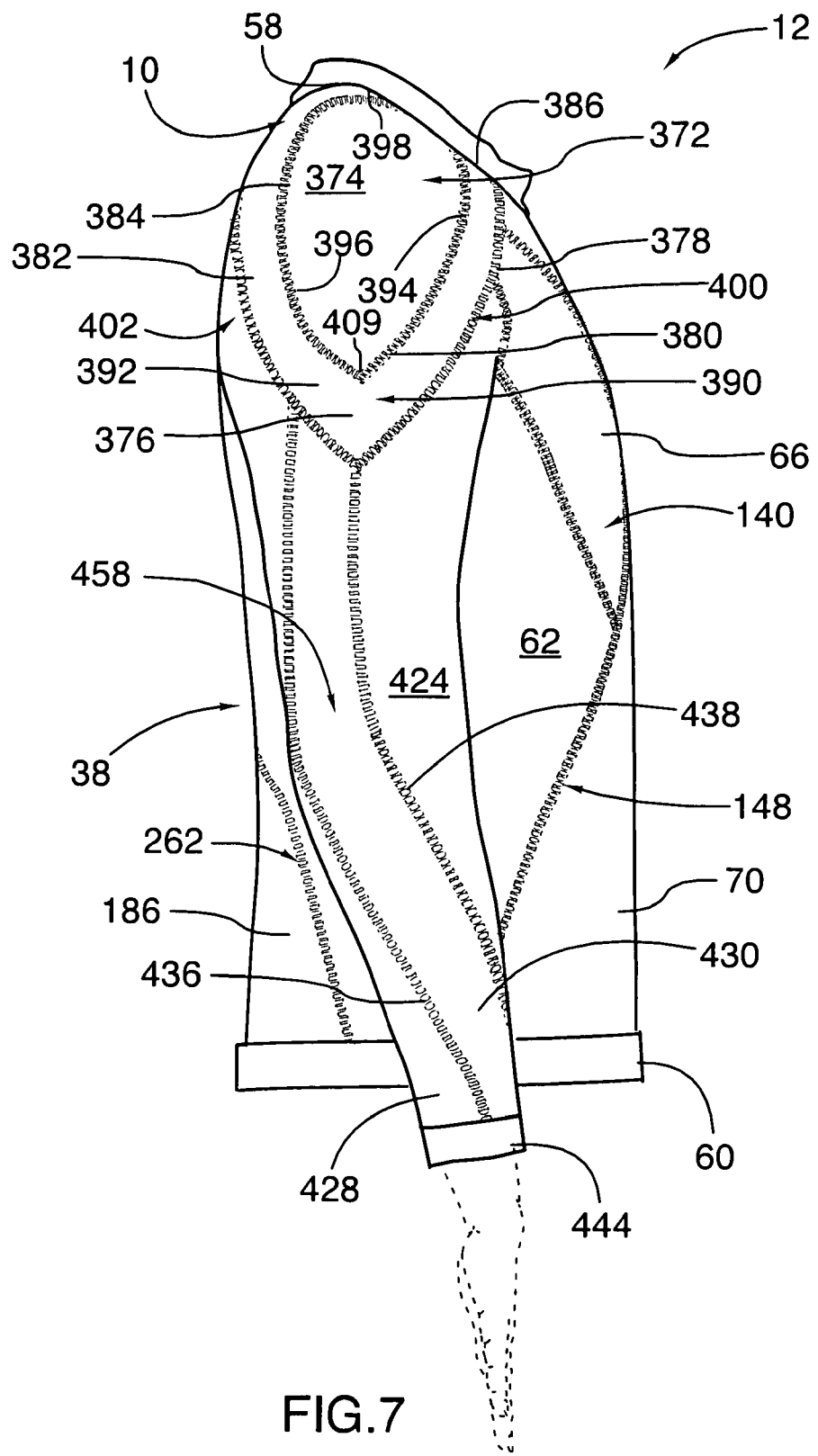
FIG. 7 is a right hand side elevation view of the wearer and the orthopedic support garment shown in FIG. 2.
Figure 8:
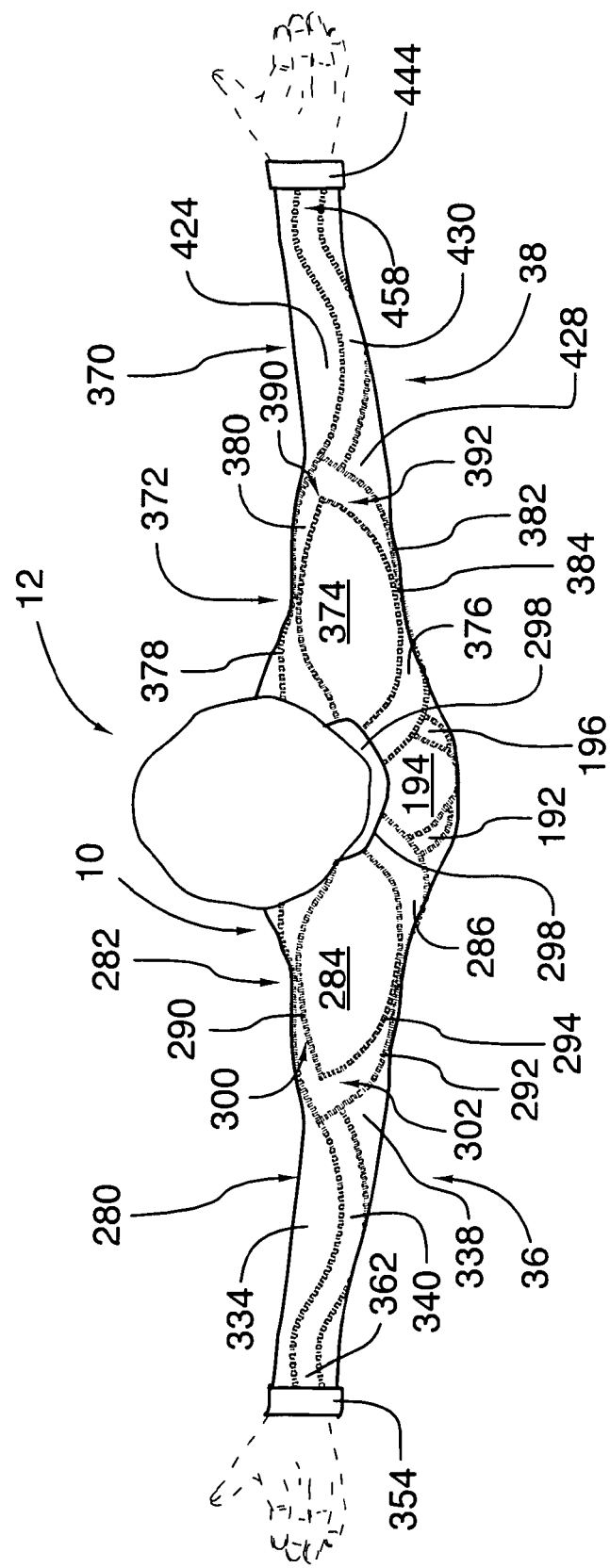
FIG. 8 is a top plan view of the wearer and the orthopedic support garment illustrated in FIG. 2, with the wearer's arms raised laterally away from the body to better reveal details of the left and right sleeve portions of the garment.

Turning to FIGS. 2 to 8, the left and right sleeve portions 36 and 38 will now be described in greater detail. The left sleeve portion 36 includes a sleeve body 280 and a shoulder part 282 disposed on the upper end of the sleeve body 280 and nestled between the collar portion 58 and each of the front and rear body portions 28 and 30. When viewed in top plan (see FIG. 8), the shoulder part 282 can be seen to have a partially truncated oval shape made up of an inner cup section 284 and an outer section 286 surrounding the inner cup section 284. As shown in FIGS. 6 and 8, the boundaries of the outer section 286 are defined by a front curved outer edge portion 288; a front curved inner edge portion 290 spaced apart from the edge portion 288; a rear curved outer edge portion 292; a rear curved inner edge portion 294 spaced apart from the edge portion 292; a first, relatively short, edge portion 296 extending between the front curved outer edge portion 288 and the front curved inner edge portion 290; and a second, relatively short, edge portion 298 (visible only in FIG. 4) extending between the rear curved outer edge portion 292 and the rear curved inner edge portion 294. The outer section 286 has a first band 300 defined between the front curved outer edge portion 288 and the front curved inner edge portion 290, and a second band 302 defined between the rear curved outer edge portion 292 and the rear curved inner edge portion 294. Each band 300, 302 is capable of functioning as a shoulder tensor band (the band 300 as a front shoulder tensor band and the band 302 as a rear shoulder tensor band), stretching (and providing resistance), when engaged by the wearer's movement.

The outer section 286 is attached to the front body portion 28 by a first seam 304 that joins the front curved outer edge portion 288 to the left upper edge portion 52, and to the rear body portion 30 by a second seam 306 that joins the rear curved outer edge portion 292 to the left upper edge portion 172 (see FIG. 6). The first and second seams 304 and 306 also serve to attach the outer section 286 to the sleeve body 280. At juncture 308, the first and second seams 304 and 306 meet.

Defining the margins of the inner cup section 284 are a front curved edge portion 314; an opposed rear curved edge portion 316; a relatively short edge 318 joining the edge portion 314 to the edge portion 316. The front curved edge portion 314 is attached to the front curved inner edge portion 292 of the outer section 286 by a third seam 312, while the rear curved edge portion 316 is attached to the rear curved inner edge portion 294 of the outer section 286 by a fourth seam 324. The third and fourth seams 312 and 324 meet at a juncture 326 (see FIG. 6). The inner cup section 284 is connected to the collar portion 58 along the short edge 318.

When the garment 10 is worn by the wearer, the shoulder part 282 locates on the wearer's left shoulder with the inner cup section 284 roughly aligned with the middle muscle fibers of the shoulder (or deltoid), the first band 300 roughly aligned with the anterior muscle fibers of the shoulder, and the second band 302 roughly aligned with the posterior muscle fibers of the shoulder. The location 312 where the first and second bands 300 and 302 meet corresponds roughly to the deltoid tuberosity of the wearer's left arm.

Figure 12:
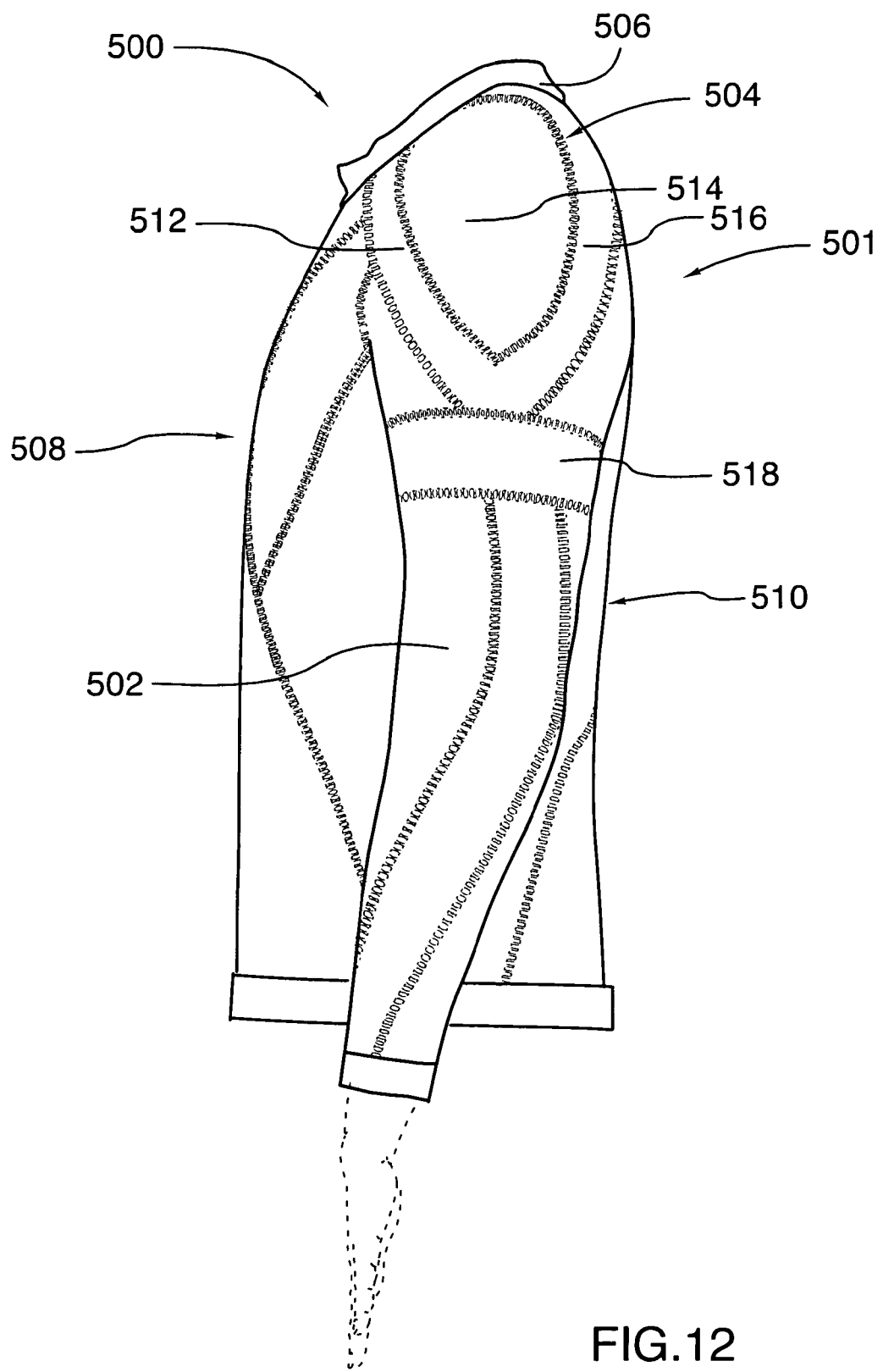
FIG. 12 is a left hand side elevation view of an orthopedic support garment in accordance with another embodiment of the present invention, the garment provided with alternate sleeve portions to those shown in FIGS. 6 and 7.

In other embodiments, the shoulder part could be configured differently. For instance, it could be formed with three clearly defined subsections corresponding to the anterior, middle and posterior heads of the deltoid (shoulder), thereby mimicking the anatomical structures of the shoulder. One such embodiment is shown in FIG. 12 wherein an alternate orthopedic support garment 500 sleeve portion is designated generally with reference numeral 501. The sleeve portion 501 is generally similar to the sleeve portion 280 in that it too includes a sleeve body 502 and a shoulder part 504. The sleeve body 502 is generally similar to the sleeve body 280 shown in FIG. 6. The shoulder part 504 is disposed on the upper end of the sleeve body 502 and nestled between the collar portion 506 and each of the front and rear body portions 508 and 510. The shoulder part 504 is made up of three elongate sections—an anterior shoulder section 512, a middle shoulder section 514 and a posterior shoulder section 516—which extend between the collar portion 506 and the sleeve body 502. The middle shoulder section 514 is disposed between, and attached to, the anterior and posterior shoulder sections 512 and 516. The shoulder part 504 is joined to the front body portion 508 along the outer edge of the anterior shoulder section 512. Similarly, the shoulder part 504 is joined to the rear body portion 510 along the outer edge of the posterior shoulder band 516. The distal ends of the shoulder sections 512, 514 and 516 converge toward each and are tied into a circumferential connector band 518 formed in the upper region of the sleeve body 502.

The insertion of the shoulder sections 512, 514 and 516 into the connector band 518 corresponds approximately to the anatomical insertion of the anterior, middle and posterior deltoid muscle fibers into the brachialis muscle. The sleeve body 502 also attaches to the circumferential connector band 518.

Referring now to FIGS. 3, 5, 6 and 8, the sleeve body 280 has a proximal end 328 and a distal end 330 and is formed by a plurality elongate fabric panels stitched together and extending from the proximal end 328 to the distal end 330. In this embodiment, the plurality of panels includes four (4) panels—a first panel 334, a second panel 336, a third panel 338 and a fourth panel 340. In other embodiments, greater or lesser number of panels could be employed to form the sleeve body. The first panel 334 is joined to the second panel 336 by a first elongate seam 342 (visible in FIG. 3); the second panel 336 is joined to the third panel 338 by a second elongate seam 344 (visible in FIG. 4); the third panel 338 is joined to the fourth panel 340 by a third elongate seam 346 (visible in FIG. 2); and the fourth panel 340 is joined to the first panel 334 by a fourth elongate seam 348 (visible in FIGS. 2 and 5). Additionally, the distal ends of the first and second panels 334 and 336 are joined to the left upper lateral edge 44 of the front body portion 28 by a first short seam 350 (visible in FIG. 3), while the distal end of the third panel 336 is joined to left upper lateral edge 164 of the rear body portion 30 by a second short seam 352 (visible in FIG. 5). In other embodiments, the number, orientation and location of the various seams could be different to match an alternate configuration of the sleeve body.

Figure 3:
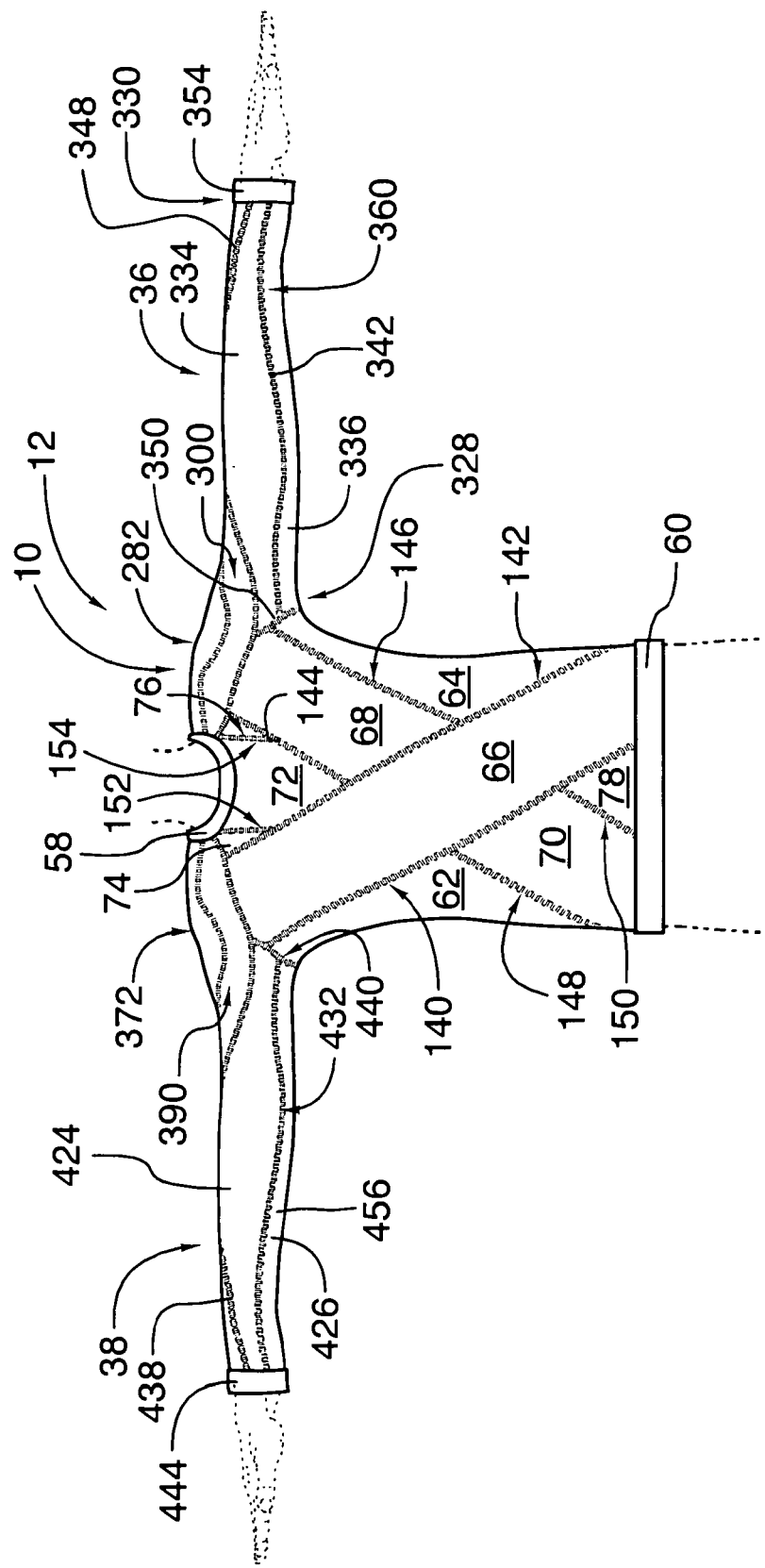
FIG. 3 is another front elevation view of the wearer and the orthopedic support garment similar to that illustrated in FIG. 2, with the wearer's arms raised laterally away from their body.

At the distal end 330 of the sleeve body 280, the panels 334, 336, 338 and 340 are attached to a sleeve cuff 354 (visible in FIGS. 3 and 5). The cuff 354 may be elasticized to snugly embrace or engage the wearer's wrist. In an alternative embodiment, the cuff could be provided with an aperture defined therethrough to permit passage of the wearer's thumb. This arrangement would tend to ensure that the sleeve body 280 remains extended and properly positioned on the wearer's arm when the garment 10 is worn.

The second and fourth panels 336 and 340 form bands 360 and 362 that are laid out in such a manner as to substantially correspond to, follow, or trace, the superficial fascia of the wearer's left arm. More specifically, the band 360 is slightly bowed and is configured to follow the superficial front arm line. When the garment 10 is worn by the wearer 12, the band 360 can be seen to be running from the wearer's left underarm to the medial epicondyle. At that location, the band 360 changes orientation and extends over the anterior side of the wearer's left forearm ultimately terminating at the anterior side of the wearer's wrist (See FIGS. 3 and 4).

The band 362 has a generally dog-legged shape and is designed to follow the superficial rear arm line 640 (shown in FIG. 1B). When the garment 10 is worn by the wearer 12, the band 362 can be seen to run from the outside of the wearer's upper arm to the lateral epicondyle. At that location, the band 362 changes orientation and extends over the posterior side of the wearer's left forearm ultimately terminating at the posterior side of the wearer's wrist (See FIGS. 5 and 6).

In this embodiment, the sleeve body 280 is provided with bands 360 and 362 which substantially trace both the superficial front arm line 624 (shown in FIG. 1A) and the superficial rear arm line 640 (shown in FIG. 1B) and which are capable of functioning as arm tensor bands, stretching (and providing resistance), when engaged by the wearer's movement. This need not be the case in every application. In an alternative embodiment, the sleeve body could be configured with a single band tracing only one of the superficial arm lines. In yet another embodiment, a pair of bands could be arranged to substantially trace both deep front and rear arm lines. Alternatively, a single band could be provided to trace only one of the deep arm lines. In a different embodiment, bands could be laid out to substantially trace one or both superficial arm lines, and one or both deep arm lines. In still another embodiment, the tensor bands could be omitted from the sleeve body.

Modifications may be brought to the left sleeve portion 36. For instance, in other embodiments, the left sleeve portion could be provided with a circumferential connector band not unlike circumferential connector band 518 shown in FIG. 12. In such a case, the circumferential connector band could be disposed between the shoulder part and the sleeve body. The bands of the shoulder part defining the front and rear shoulder tensor bands could tie into the circumferential connector band. Similarly, the various panels of the sleeve body could be attached to the circumferential connector band.

Referring to FIGS. 2 to 5, 7 and 8, the right sleeve portion 38 resembles the left sleeve portion 36 in that it too includes a sleeve body 370 and a shoulder part 372 disposed on the upper end of the sleeve body 370 and nestled between the collar portion 58 and each of the front and rear body portions 28 and 30. When viewed in top plan, the shoulder part 372 can be seen to have a partially truncated oval shape made up of an inner cup section 374 and an outer section 376 surrounding the inner cup section 374. The boundaries of the outer section 376 are defined by a front curved outer edge portion 378; a front curved inner edge portion 380 spaced apart from the edge portion 378; a rear curved outer edge portion 382; a rear curved inner edge portion 384 spaced apart from the edge portion 382; a first, relatively short, edge portion 386 extending between the front curved outer edge portion 378 and the front curved inner edge portion 380; and a second, relatively short, edge portion 388 extending between the rear curved outer edge portion 382 and the rear curved inner edge portion 384. The outer section has a first band 390 defined between the front curved outer edge portion 378 and the front curved inner edge portion 380, and a second band 392 defined between the rear curved outer edge portion 382 and the rear curved inner edge portion 384. Each band 390, 392 is capable of functioning as a shoulder tensor band (the band 390 as a front shoulder tensor band and the band 392 as a rear shoulder tensor band), stretching (and providing resistance), when engaged by the wearer's movement.

The outer section 376 is attached to the front body portion 28 by a first seam 400 that joins the front curved outer edge portion 378 to the right upper edge portion 54, and to the rear body portion 30 by a second seam 402 that joins the rear curved outer edge portion 382 to the right upper edge portion 174 (see FIG. 7). The first and second seams 400 and 402 also serve to attach the outer section 386 to the sleeve body 370. At juncture 404, the first and second seams 400 and 402 meet.

Defining the margins of the inner cup section 374 are a front curved edge portion 394; an opposed rear curved edge portion 396; a relatively short edge 398 joining the edge portion 394 to the edge portion 396. The front curved edge portion 394 is attached to the front curved inner edge portion 382 of the outer section 376 by a third seam 406, while the rear curved edge portion 396 is attached to the rear curved inner edge portion 384 of the outer section 376 by a fourth seam 408. The third and fourth seams 406 and 408 meet at a juncture 409. The inner cup section 374 is connected to the collar portion 58 along the short edges 398.

When the garment 10 is worn by the wearer, the shoulder part 372 locates on the wearer's right shoulder with the inner cup section 374 roughly aligned with the middle muscle fibers of the shoulder (or deltoid), the first band 390 roughly aligned with the anterior muscle fibers of the shoulder, and the second band 392 roughly aligned with the posterior muscle fibers of the shoulder. The location 402 where the first and second bands 390 and 392 meet corresponds roughly to the deltoid tuberosity of the wearer's right arm.

A person skilled in the art will appreciate that modifications similar to those described above in the context of the shoulder part 282, could also be brought to the shoulder part 372 such that there is no need to repeat the description thereof here.

Referring now to FIGS. 3, 4, 5, 7 and 8, the sleeve body 370 is generally similar to the sleeve body 280 described above. It has a proximal end 410 and a distal end 412 and is formed by a plurality elongate fabric panels stitched together and extending from the proximal end 410 to the distal end 412. In this embodiment, the plurality of panels includes four (4) panels—a first panel 424, a second panel 426, a third panel 428 and a fourth panel 430. In other embodiments, greater or lesser number of panels could be employed to form the sleeve body. The first panel 424 is joined to the second panel 426 by a first elongate seam 432 (visible in FIG. 3); the second panel 426 is joined to the third panel 428 by a second elongate seam 434 (visible in FIG. 4); the third panel 428 is joined to the fourth panel 430 by a third elongate seam 436 (visible in FIGS. 4 and 5); and the fourth panel 430 is joined to the first panel 424 by a fourth elongate seam 438 (visible in FIGS. 2 and 5). Additionally, the distal ends of the first and second panels 424 and 426 are joined to the right upper lateral edge 46 of the front body portion 28 by a first short seam 440 (visible in FIG. 3), while the distal end of the third panel 428 is joined to right upper lateral edge 166 of the rear body portion 30 by a second short seam 442 (visible in FIG. 5). In other embodiments, the number, orientation and location of the various seams could be different to match an alternate configuration of the sleeve body.

At the distal end 412 of the sleeve body 370, the panels 424, 426, 428 and 430 are attached to a sleeve cuff 444. The cuff 444 may be elasticized to snugly embrace or engage the wearer's wrist. As is the case with 352, cuff 444 could be provided with an aperture defined therethrough to permit passage of the wearer's thumb. This arrangement would tend to ensure that the sleeve body 370 remains extended and properly positioned on the wearer's arm when the garment 10 is worn.

The second and fourth panels 426 and 430 form bands 456 and 458 that are laid out in such a manner as to substantially correspond to, follow, or trace, the superficial fascia of the wearer's left arm, and capable of functioning as arm tensor bands, stretching (and providing resistance), when engaged by the wearer's movement. The band 456 is slightly bowed and is configured to follow the superficial front arm line 624 (shown in FIG. 1B). When the garment 10 is worn by the wearer 12, the band 456 can be seen to be running from the wearer's right underarm to the medial epicondyle. At that location, the band 456 changes orientation and extends over the anterior of the wearer's right forearm ultimately terminating at the anterior side of the wearer's wrist (see FIGS. 3 and 4).

The band 458 has a generally dog-legged shape and is designed to follow the superficial rear arm line 640 (show in FIG. 1B). When the garment 10 is worn by the wearer 12, the band 458 can be seen to run from the outside of the wearer's upper arm to the lateral epicondyle. At that location, the band 458 changes orientation and extends over the posterior side of the wearer's right forearm ultimately terminating at the posterior side of the wearer's wrist (see FIGS. 5 and 7).

In like fashion to the sleeve body 280, the sleeve body 370 could be configured with a different number and/or arrangement of bands. An alternate sleeve body could have a single band substantially tracing one of the superficial or deep arm lines, or could have multiple bands substantially tracing one or more of the superficial arm lines and one or more of the deep arm lines.

Modifications similar to those discussed in the context of the left sleeve portion 36, could be brought to the right sleeve portion 38 as well.

Referring to FIGS. 3 and 5, the waistband portion 60 can be seen to extend circumferentially about the lowermost margin of the garment. The waistband portion is elasticized and also includes friction enhancing means on its underside. In this embodiment, the friction enhancing means take the form of a plurality of very small rubber loops or nubs (not shown) that depend from the waistband portion. The loops are designed to frictionally engage the surface against which they bear. This arrangement tends to hold the orthopedic support garment 10 in place thereby preventing the garment 10 from lifting up as the wearer moves. In this embodiment, the garment 10 is configured so that the waistband portion 60 rides at hip level on the wearer. In other embodiments, the garment 10 could be worn higher or lower on the wearer.

The garment 10 and the various panels of the front and rear body portions 28 and 30, and the left and right sleeve portions 36 and 38 are fabricated from an elastic or stretchable fabric selected to provide a tight, compression-like (or form-fitting) fit on the wearer. Preferably, the fabric would have four-way stretch. However, in certain cases, a fabric having two-way stretch could be employed. The fabric could contain one or more of polyester, spandex, elastic, nylon, or the like.

In the embodiment shown in FIGS. 2 to 10, the garment is constructed of fabrics exhibiting different stiffness, resistance or elasticity characteristics. More specifically, different fabrics have been employed for different panels depending on the desired resistance to movement to be created by the panel. The panels 66, 68, 70, 186, 188, and 190 which function as tensor bands on the front and rear body portions 28 and 30 are made of an elastic cotton material. The other panels 62, 64, 72, 74, 76, 78, 182, 184, 192, 194, 196 and 198 that make up the front and rear body portions 28 and 30 are made of a less stiff fabric exhibiting greater elastic properties than the fabric used for the front and rear body tensor bands. The fabric used for these latter panels may be a combination of nylon, spandex and polyester.

Regarding the right and left sleeve portions 36 and 38, the panels 336, 340, 426 and 430 which define the right and left arm tensor bands, and the bands 300, 302, 390 and 392 which define the right and left front and rear shoulder tensor bands, are made from a stiffer or heavier fabric than that used for the front and rear body tensors. For example, one or more of the right and left arm tensor bands and the right and left shoulder tensor bands could be made with OMNI-SKYN™ produced by BodyHelix, LLC, in Greensboro, N.C. Advantageously, such fabric tends to grip the wearer's skin for further enhanced proprioception.

Optionally, one or more of the front and rear body tensor bands, the arm tensor bands or the shoulder tensor bands could be provided with a textured or friction-enhancing surface on their underside for contact with the wearer's skin. In a further alternative, the underside of these tensor bands could have small projecting nubs or other like structures for bearing against the wearer's skin. Such friction-enhancing surfaces or projecting nubs could be provided to heighten the proprioception experienced by the wearer.

It will thus be appreciated that by selecting fabrics of varying stiffness and elasticity greater or lesser resistance of movement may be provided to accommodate the wearer's physical condition. In this way, the garment can be made to suit a patient which is rehabilitating from injury, or an athlete seeking to improve his/her conditioning, proprioceptive function.

In alternative embodiments, all the panels of the garment could be made using the same fabric.

For enhanced comfort for the wearer, it is preferred that the fabrics used in the garment be breathable and have moisture wicking properties. In this regard, the fabrics may have incorporated therein metal ions, or other mechanical sweat wicking, temperature regulating materials.

In this embodiment, flat-lock stitching is used to form the seams 140 to 154, 260 to 274, 304, 306, 312, 324, 342 to 352, 400, 402, 408 and 432 to 442. In other embodiments, a different type of stitching could be used. While in the embodiment described, the various panels are sewn to each other. In other embodiments, the panels could be attached to each other differently, of further still the panels could be merged or incorporated with each other using advanced production techniques.

Having described the structure of the orthodontic support garment 10 and its constituent parts, what follows is a brief description of how the various tensor bands formed in the garment 10 may be engaged by the wearer's movements. Only a few basic movements are described to illustrate the engagement of the tensors. These movements are representative only. Accordingly, the description of the engagement of the tensor bands is not intended to be exhaustive or limiting and is merely provided to enhance comprehension.

Figure 13A:
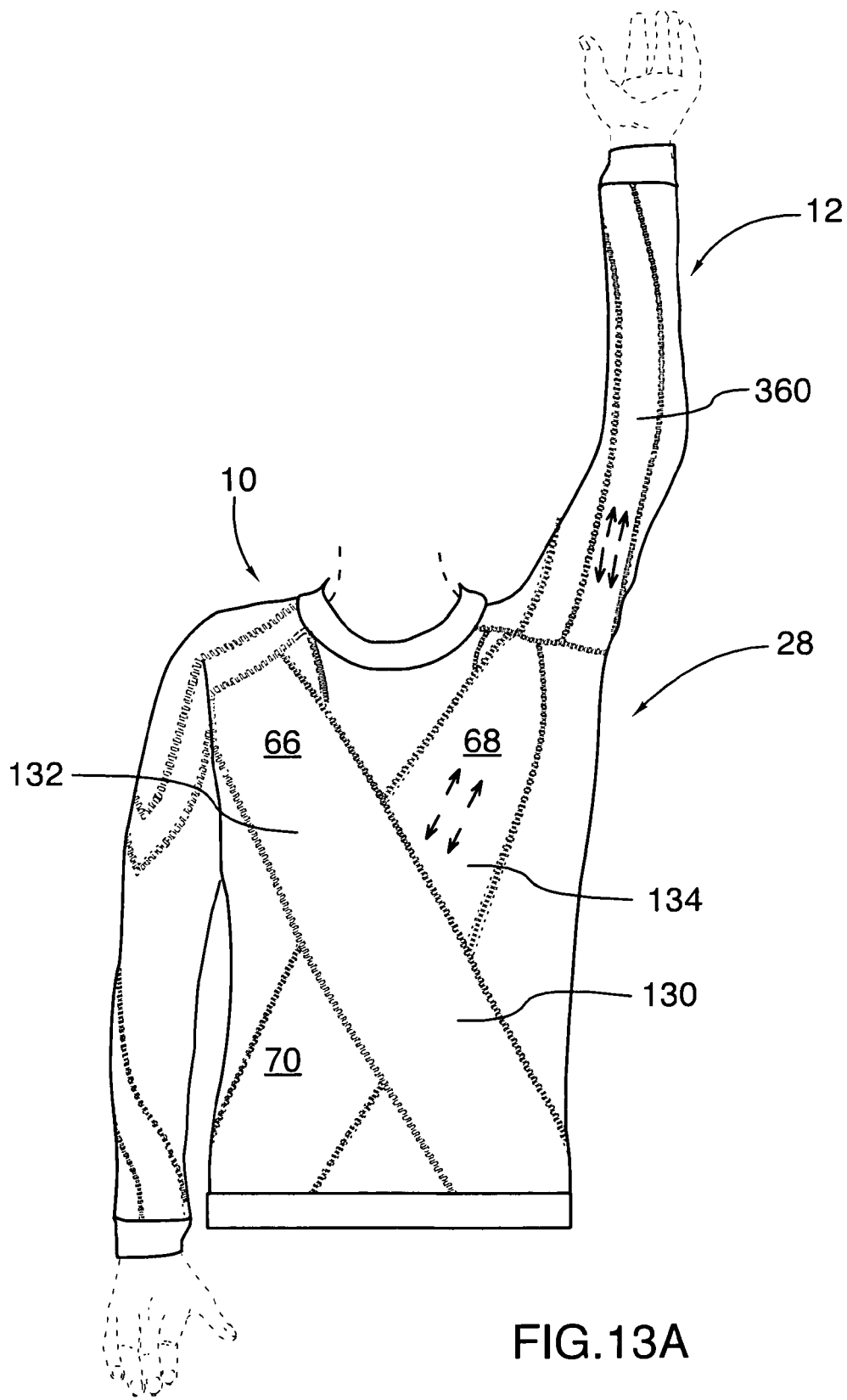
FIG. 13a is a front elevation view of the wearer and the orthopedic support garment shown in FIG. 2 showing the wearer's left arm raised overhead.
Figure 13B:
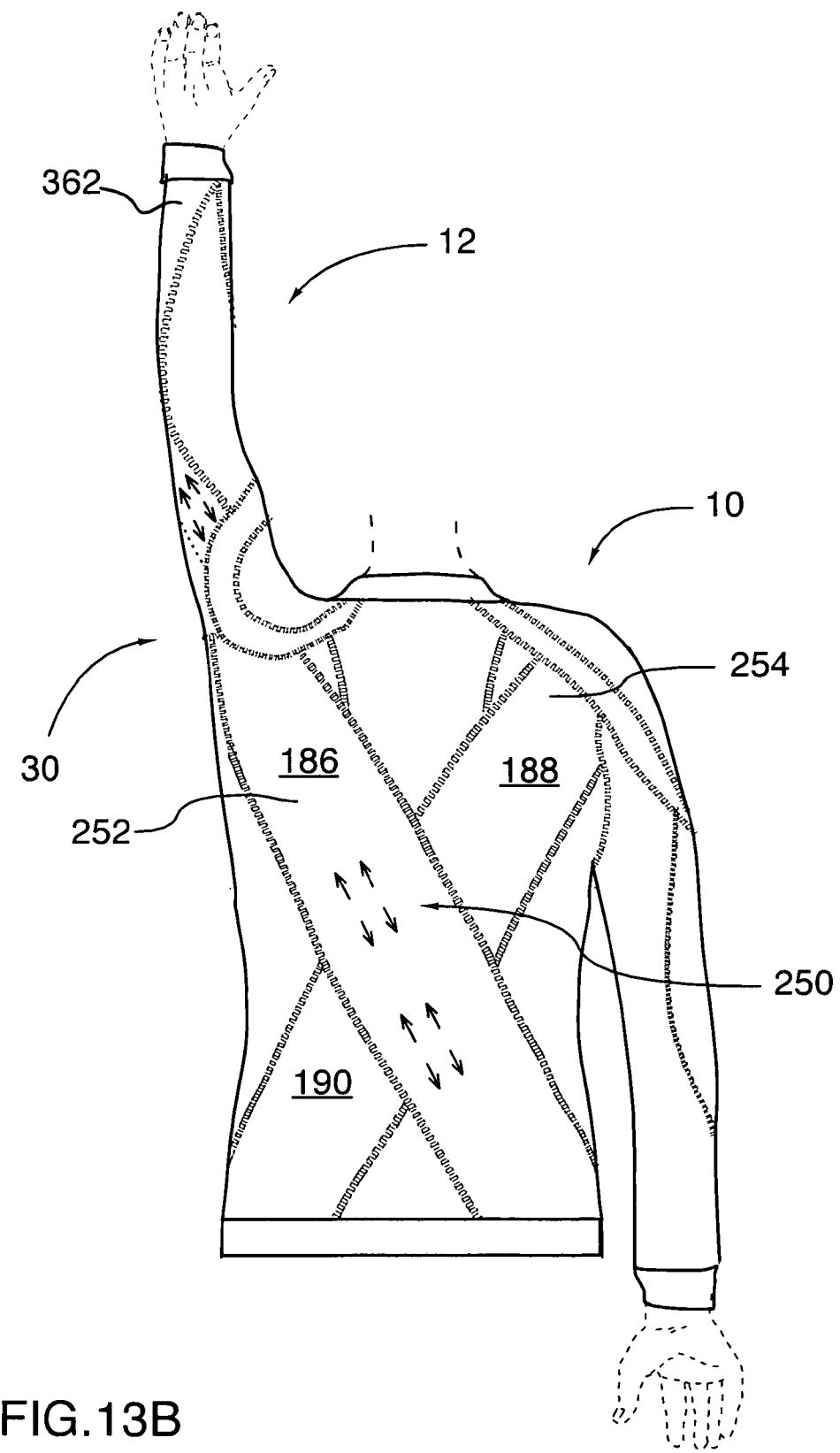
FIG. 13b is a rear elevation view of the wearer and the orthopedic support garment illustrated in FIG. 2 showing the wearer's left arm raised overhead.

FIGS. 13A and 13B show the wearer 12 of the garment 10 with his/her left arm raised above his/her head. It can be seen that in that position, the second diagonally-extending panel 68 of the front panel 28 is extended or stretched (as depicted by the arrows) and that consequently, the front diagonal tensor band defined by the second arm 134 of the cross-like structure 130 is engaged (see FIG. 13A), mimicking the engagement of the front functional line 630 in the wearer's anatomy. In FIG. 13A, the tensor band 360 can also be seen to be in tension (as depicted by the arrows) in a manner not unlike the engagement of the superficial front arm line 624.

Similarly, when the wearer 12 is in that position, the first diagonally-extending panel 186 of the rear panel 30 is extended or stretched and the rear diagonal tensor band defined by the first arm 252 of the cross-like structure 250 is engaged (see FIG. 13B), imitating the engagement of the back functional line 630 in the wearer's anatomy. In FIG. 13B, the tensor band 362 can also be seen to be in tension in a manner not unlike the engagement of the superficial rear arm line 640.

Figure 14:
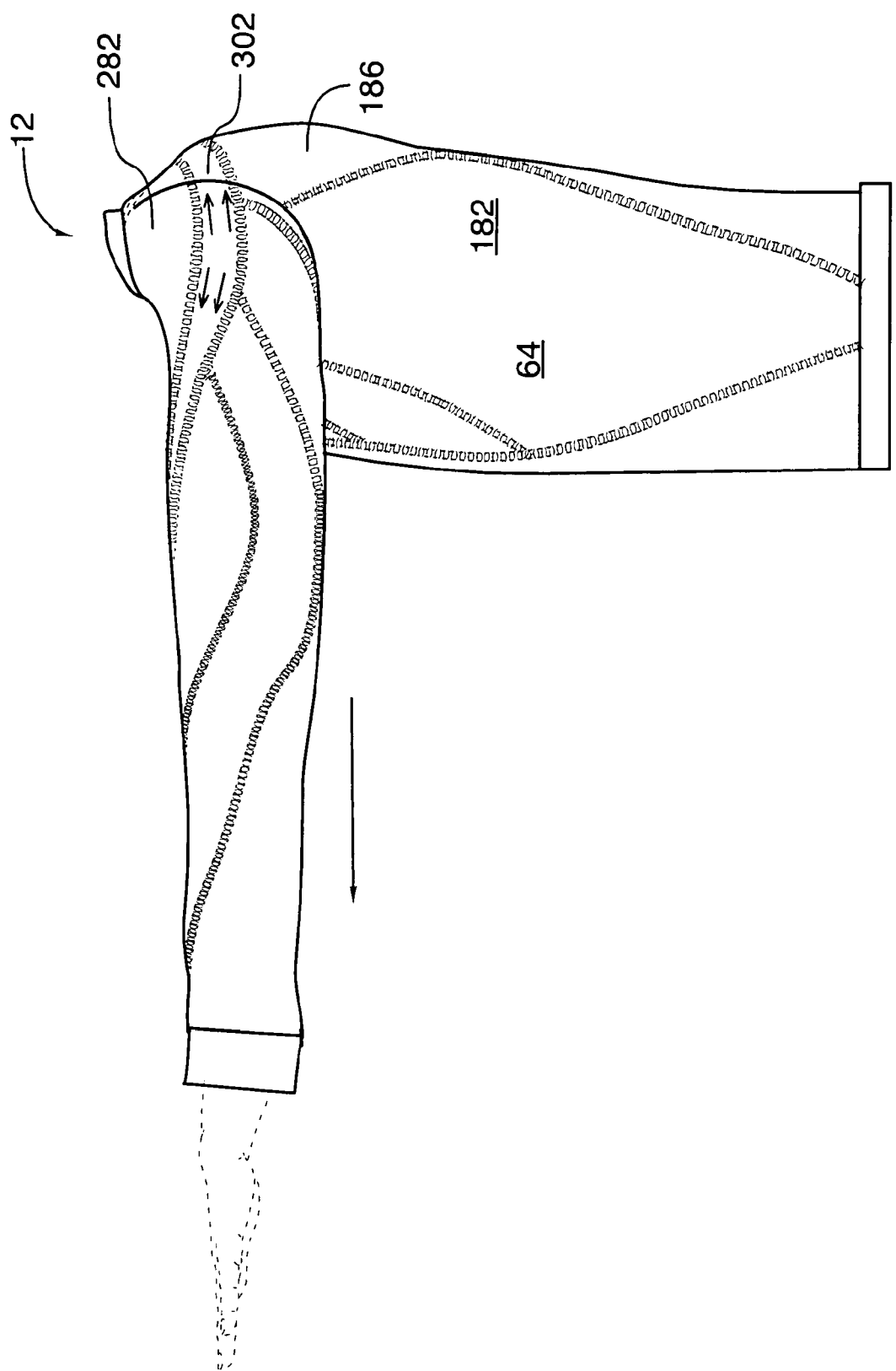
FIG. 14 is a left side elevation view of the wearer and the orthopedic support garment illustrated in FIG. 2 showing the wearer's left arm raised to shoulder level and forwardly extended.

FIG. 14 shows the wearer 12 of the garment 10 with his/her left arm raised to shoulder level and forwardly extended. In that position, it can be seen that the rear shoulder tensor band defined by the second band 302 of the shoulder part 282 is engaged. In addition, the first diagonally-extending panel 186 (defining one of the rear diagonal tensor bands) can be seen to be in tension, imitating the engagement of the back functional line 630 in the wearer's anatomy.

Figure 15:
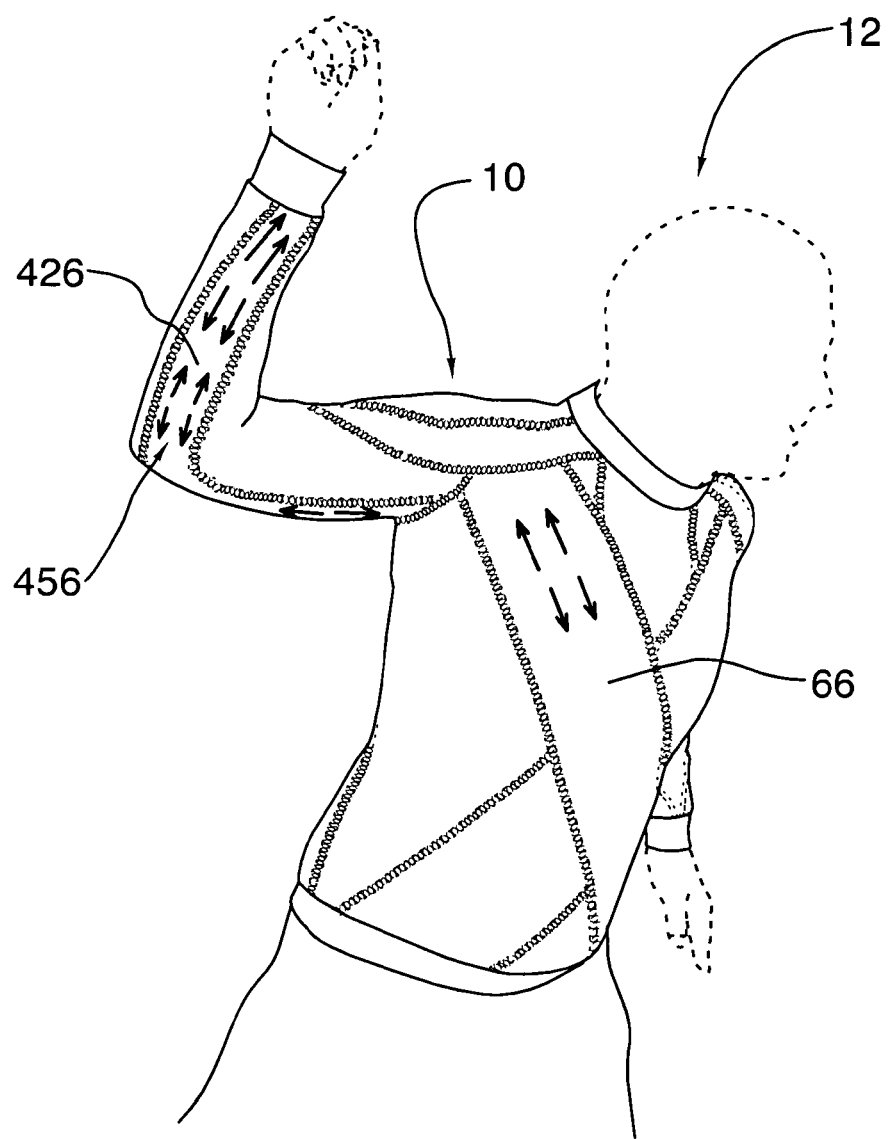
FIG. 15 is a front perspective view of the wearer and the orthopedic support garment illustrated in FIG. 2 showing the wearer's right arm lifted overhead in the cocking phase position which precedes a baseball pitcher's throw.

FIG. 15 shows the wearer 12 of the garment 10 with his/her right arm overhead in the cocking phase position preceding a baseball pitcher's throw. In that position, it can be seen that the right arm tensor 456 defined by the second panel 426 is engaged, mimicking the anatomical engagement of the superficial front arm line 624. In addition, the first diagonally-extending panel 66 (defining one of the front diagonal tensor bands) can be seen to be in tension, imitating the engagement of the front functional line 610 in the wearer's anatomy.

FIG. 16 shows the wearer 12 of the garment 10 with his/her right arm fully extended in the release phase position following a baseball pitcher's throw. In that position, it can be seen that the right arm tensor 458 defined by the fourth panel 430 is engaged, mimicking the anatomical engagement of the superficial rear arm line 640. In addition, the second diagonally-extending panel 188 (defining one of the rear diagonal tensor bands) can be seen to be in tension, imitating the engagement of the back functional line 630 in the wearer's anatomy.

While in the embodiment shown in FIGS. 2 to 10 the garment 10 takes the form of a long-sleeved shirt, it should be appreciated that in other embodiments, it could take a different form. Applying the principles of the present invention with appropriate modifications, the orthopedic support garment could be configured as a t-shirt, a bodysuit, a jumpsuit, or any similar garment. Additionally, the garment could be worn as stand alone athletic wear or could be used as an underlayer to be worn beneath clothing or equipment.

It will thus be appreciated that by having various tensor panels disposed along certain key fascial planes or lines of the body, the garment is able to elicit an enhanced anatomically appropriate proprioceptive (and kinesthetic) feedback to the wearer for various muscle groups of the upper body during the wearer's movement. This proprioceptive feedback can be useful for teaching athletes in a variety of sports, the proper phases of a movement.

Although the foregoing description and accompanying drawings relate to specific preferred embodiments of the present invention as presently contemplated by the inventor, it will be understood that various changes, modifications and adaptations, may be made without departing from the spirit of the invention.

What is claimed is:

1. A long-sleeved shirt orthopedic garment comprising:
   a garment body having a front body portion, a rear body portion joined to the front body portion along right and left lateral portions and along right and left upper edge portions, a waistband extending circumferentially about lower margins of the front and rear body portions, and right and left long-sleeve portions attached to the front and rear body portions proximate the respective right and left upper edge portions, the left and right sleeve portions including respective first and second cuffs configured to extend around respective wrists of a wearer;
   a first tensor band laid out along one of the front and rear body portions having a first end extending from the waistband adjacent one of the right and left lateral portions diagonally to a second end at the opposite left or right upper edge portion; and
   a first arm tensor band having a first end extending from one of the first and second cuffs to a second end at the first tensor band.

2. The long-sleeved shirt orthopedic garment of claim 1, further comprising:
a first tensor band extending upwardly from a first end proximate the lower margin of one of the front and rear body portions to a second end disposed at least as high as an upper edge of the right and left lateral portions.

3. The long-sleeved shirt orthopedic garment of claim 2, wherein the first tensor band extends diagonally from the first end to the second end.

4. The long-sleeved shirt orthopedic garment of claim 3, wherein the second end is disposed at the upper edge of one of the right and left lateral portions.

5. The long-sleeved shirt orthopedic garment of claim 2, further comprising:
a second tensor band extending upwardly from a first end proximate the lower margin of one of the front and rear body portions to a second end disposed at least as high as an upper edge of the right and left lateral portions.

6. A long-sleeved shirt orthopedic garment comprising:
a garment body having a front body portion, a rear body portion joined to the front body portion along right and left lateral portions and along right and left upper edge portions, and right and left long-sleeve portions attached to the front and rear body portions proximate the respective right and left upper edge portions, the front and rear body portions each including an intermediate upper edge portion disposed between the right and left upper edge portions, the left and right sleeve portions each including first ends configured to extend around respective wrists of a wearer;
a collar portion attached to the intermediate upper edge portions;
a first arm tensor band extending from the first end of the right sleeve portion to the collar portion; and
a second arm tensor band extending from the first end of the left sleeve portion to the collar portion.

7. The long-sleeved shirt orthopedic garment of claim 6, further comprising:
a first tensor band extending from a first end proximate a lower margin of one of the front and rear body portions to a second end at the opposite left or right upper edge portion.

8. The long-sleeved shirt orthopedic garment of claim 7, further comprising:
a waistband extending circumferentially about the lower margins of the front and rear body portions;
wherein the first end of the first tensor band is disposed proximate the waistband.

9. The long-sleeved shirt orthopedic garment of claim 7, further comprising:
a second tensor band extending from a first end proximate the lower margin of one of the front and rear body portions to a second end at the opposite left or right upper edge portion.

10. A long-sleeved shirt orthopedic garment comprising:
a garment body having a front body portion, a rear body portion joined to the front body portion along right and left lateral portions and along right and left upper edge portions, and right and left long-sleeve portions attached to the front and rear body portions proximate the respective right and left upper edge portions, the left and right sleeve portions including respective distal ends configured to extend around respective wrists of a wearer;
a first tensor band extending upwardly from a first end proximate the lower margin of one of the front and rear body portions to a second end disposed at least as high as an upper edge of the right and left lateral portions;
a second tensor band extending upwardly from a first end proximate the lower margin of one of the front and rear body portions to a second end disposed at least as high as the upper edge of the right and left lateral portions.

11. The long-sleeved shirt orthopedic garment of claim 10, further comprising:
the front and rear body portions each including an intermediate upper edge portion disposed between the right and left upper edge portions;
a collar portion attached to the intermediate upper edge portions;
a first arm tensor band extending from the first end of the right sleeve portion to the collar portion; and
a second arm tensor band extending from the first end of the left sleeve portion to the collar portion.

12. The long-sleeved shirt orthopedic garment of claim 10, further comprising:
a waistband extending circumferentially about the lower margins of the front and rear body portions;
wherein the first ends of the first and second tensor bands are proximate the waistband.

13. The long-sleeved shirt orthopedic garment of claim 10, wherein the first and second tensor bands extend diagonally from the first ends to the second ends.

14. The long-sleeved shirt orthopedic garment of claim 13, wherein the second ends of the first and second tensor bands are adjacent the right and left lateral portions, respectively.

15. The long-sleeved shirt orthopedic garment of claim 14, wherein the first ends of the first and second tensor bands are adjacent the left and right lateral portions, respectively.

* * * * *